(12) United States Patent
Zampieri et al.

(10) Patent No.: US 8,586,598 B2
(45) Date of Patent: Nov. 19, 2013

(54) CDK INHIBITOR SALTS

(75) Inventors: Massimo Zampieri, Cesano Maderno (IT); Annalisa Airoldi, Nosate (IT); Maria Gioia Fornaretto, Milan (IT); Maria Gabriella Brasca, Cusago-Milan (IT)

(73) Assignee: Nerviano Medical Sciences S.R.L., Nerviano (MI) (IT)

( * ) Notice: Subject to any disclaimer, the term of this patent is extended or adjusted under 35 U.S.C. 154(b) by 0 days.

(21) Appl. No.: 13/265,918

(22) PCT Filed: Apr. 23, 2010

(86) PCT No.: PCT/EP2010/055463
§ 371 (c)(1),
(2), (4) Date: Oct. 24, 2011

(87) PCT Pub. No.: WO2010/125004
PCT Pub. Date: Nov. 4, 2010

(65) Prior Publication Data
US 2012/0041007 A1    Feb. 16, 2012

(30) Foreign Application Priority Data
Apr. 29, 2009  (EP) .................................... 09159030

(51) Int. Cl.
*A61K 31/505* (2006.01)
*C07D 491/00* (2006.01)

(52) U.S. Cl.
USPC .......................................... 514/267; 544/251

(58) Field of Classification Search
USPC .......................................... 514/267; 544/251
See application file for complete search history.

(56) References Cited

FOREIGN PATENT DOCUMENTS

| WO | WO 2004/104007 A1 | 12/2004 |
|---|---|---|
| WO | WO 2007/090794 A1 | 8/2007 |
| WO | WO 2007090794 A1 * | 8/2007 |

OTHER PUBLICATIONS

Gray, N, et al. "ATP-site directed inhibitors of cyclin-dependent kinases." Curr. Med. Chem. 6(9), (Sep. 1999), pp. 859-875.*
Shapiro, G.I. "Cyclin-Dependent Kinase Pathways As Targets for Cancer Treatment." Journal of Clinical Oncology. vol. 24, No. 11, (Apr. 10, 2006), pp. 1770-1783.*
Braun-Dullaeus, R.C., et al. "Cell Cycle Progression: New Therapeutic Target for Vascular Proliferative Disease." Circulation. vol. 98, (1998), pp. 82-89.*
Kumar, L, et al. "Salt Selection in Drug Development." PharmTech. com. Mar. 2, 2008.*
Sheth, A.R., et al. "Relationship between the Structure and Properties of Pharmaceutical Crystals." KONA. No. 23 (2005), pp. 36-48.*
International Search Report dated Jun. 8, 2010 issued in PCT/EP2010/055463.

* cited by examiner

*Primary Examiner* — Noble Jarrell
*Assistant Examiner* — John S Kenyon
(74) *Attorney, Agent, or Firm* — Scully, Scott, Murphy & Presser, P.C.

(57) ABSTRACT

The present invention relates to novel crystalline form(s) of water-soluble salts and of free base of a cdk inhibitor. Such crystal salts are for example fumarate, L-malate, maleate, succinate, adipate, malonate, glycolate, phosphate, mesylate, L-lactate, hydrochloride, di-hydrochloride, tri-hydrochloride. Hydrates and polymorphs of such new salt forms, a process for their preparation, their utility in therapy and to the pharmaceutical compositions containing them are also claimed and described in the present application.

6 Claims, 21 Drawing Sheets

CDK INHIBITOR SALTS

The present invention relates to novel crystalline, water-soluble salts of a cdk inhibitor, to a process for their preparation, to hydrates and polymorphs of such new salt forms, to their utility in therapy and to pharmaceutical compositions containing them.

It is well known that progression through the cell cycle is governed by a series of checkpoint controls, otherwise referred to as restriction points, which are regulated by a family of enzymes known as the cyclin-dependent kinases (cdks). In turn, the cdks themselves are regulated at many levels such as, for instance, binding to cyclins.

The coordinated activation and inactivation of different cyclin/cdk complexes is necessary for normal progression through the cell cycle. Both the critical G1-S and G2-M transitions are controlled by the activation of different cyclin/cdk activities. In G1, both cyclin D/cdk4 and cyclin E/cdk2 are thought to mediate the onset of S-phase. Progression through S-phase requires the activity of cyclin A/cdk2 whereas the activation of cyclin A/cdc2 (cdk1) and cyclin B/cdc2 are required for the onset of mitosis. For a general reference to cyclins and cyclin-dependent kinases see, for instance, Kevin R. Webster et al, in Exp. Opin. Invest. Drugs, 1998, Vol. 7(6), 865-887.

Checkpoint controls are defective in tumor cells due, in part, to disregulation of cdk activity. For example, altered expression of cyclin E and cdks has been observed in tumor cells, and deletion of the cdk inhibitor p27 KIP gene in mice has been shown to result in a higher incidence of cancer.

Increasing evidence supports the idea that the cdks are rate-limiting enzymes in cell cycle progression and, as such, represents molecular targets for therapeutic intervention. In particular, the direct inhibition of cdk/cyclin kinase activity should be helpful in restricting the unregulated proliferation of a tumor cell. Some pyrazoloquinazolines have been demonstrated to be potent inhibitors of cyclin dependent kinase enzymes, particularly cdk2. One of these compounds is currently in development as an anti-cancer agent. Cdks inhibitors are understood to block passage of cells from the G2/M phase of the cell cycle.

It is an object of the invention to provide, in a first aspect, a salt of the compound 125 having the following formula:

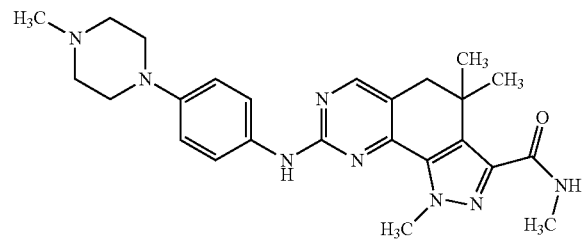 [SMILES: CNC(=O)c1nn(C)c2c1C(C)(C)Cc1cnc(Nc3ccc(N4CCN(C)CC4)cc3)nc1-2]

In the present description, unless otherwise specified, the compound 125 is 8-[4-(4-methyl-piperazin-1-yl)-phenylamino]-1,4,4-trimethyl-4,5-dihydro-1H-pyrazolo[4,3-h]quinazoline-3-carboxylic acid methylamide. It can be prepared as described in the international patent application WO 2004104007 published on Feb. 12, 2004, and is endowed with protein kinase inhibitory activity and is thus useful in therapy as antitumor agent. In particular, the preferred preparation of the compound 125 is that described in example 58 of the above mentioned International Patent Application.

The International patent application WO2007090794 published on 16.8.2007 describes and claims specific synergic combination of such compound with other antitumor agents.

The compound 125 is a poorly water-soluble compound, which shows aqueous solubility of less than 0.1 mg/ml. The solubility of the compound 125 in 5% dextrose solution is lower than 0.1 mg/ml, about 0.8 mg/ml in aqueous 10% Polysorbate 80, about 8 mg/ml in aqueous 50% Polyethylene Glycol 400 and about 10 mg/ml or higher when formulated as HCl in situ salt.

Furthermore, the free base is slightly hygroscopic since showing a maximum uptake of about 2% of water at 90% relative humidity (RH) at 25° C.

The initially obtained free base was converted into the tri-hydrochloride salt in order to improve solubility of the compound and allow formulating the drug as aqueous solution (solubility of about 10 mg/ml in 5% dextrose solution) for early pharmacological and toxicological evaluation (as described in example 59 of the above mentioned International Patent Application).

Though solving the problem of the early formulation approach, the obtained tri-hydrochloride salt was an amorphous hygroscopic solid, thus not suitable for development of an oral formulation.

Moisture uptake is a significant concern for pharmaceutical powders. Moisture has been shown to have a significant impact, for example, on the physical, chemical and manufacturing properties of drugs, excipients and formulations. It is also a key factor in taking decisions related to packaging, storage, handling and shelf life and successful development requires a sound understanding of hygroscopic properties.

For instance, conversion from an anhydrous to a hydrate form may be observed when the relative humidity exceeds a critical level and moisture content rapidly increases in the solid. This has not only an impact on the physical and pharmaceutical properties of the drug per se, but also on its biopharmaceutical perspective. Moreover, it is well known, that hydrate forms usually tends to be less soluble with respect to a homologous anhydrous form, with potential detrimental effect also on the dissolution rate properties of the active compound per se and on its absorption profile through the gastrointestinal tract. At the same manner, conversion from a crystalline to an amorphous form may be observed in presence of humidity, with potential disadvantages in terms of physical stability. The amorphous active drug substance, if deliquescent, can for instance absorb relatively large amounts of water from the atmosphere up to its dissolution while also its chemical stability can be affected since the amorphous structure, being thermodynamically activated, is more prone to chemical degradation and to chemical interaction with other chemical species. Thus the performance and the efficacy of both formulation and active ingredient may be significantly changed.

Accordingly, there is a need in therapy of a water-soluble salt of the compound 125 endowed with lower hygroscopicity and good and reproducible biopharmaceutical properties for allowing a safer and efficacious oral administration.

The present inventors have solved the above-described technical problem by providing novel salts as well as novel crystal form of salts of the compound 125 having improved physicochemical properties. In fact, the novel salts are crystalline, less hygroscopic, rapidly-dissolving solids with high water solubility and substantially introducing important advantages in handling, storage and formulations etc., in addition to possessing all the other advantages, in particular therapeutic advantages, exhibited by the known form of amorphous free base and tri-hydrochloride salt.

Surprisingly, new salt and free base forms of the compound 125 were found and proven to be crystalline. The property of being crystalline powders renders these forms particularly suitable for pharmaceutical development.

BRIEF DESCRIPTION OF THE DRAWINGS

The invention is also illustrated by reference to the accompanying drawings described below.

Figure 1:
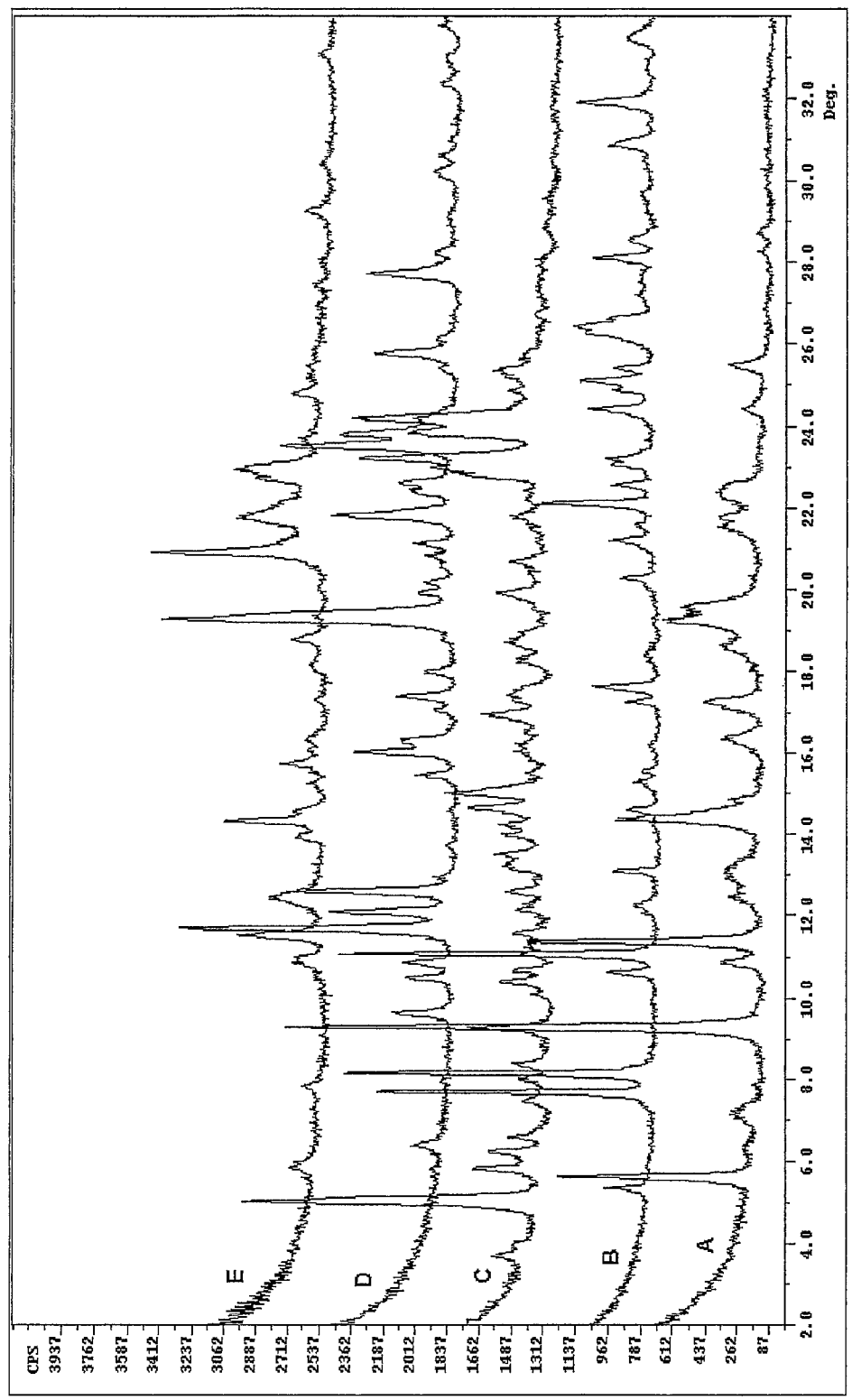
FIG. 1 shows the X-ray diffractograms of compound 125 free base and its crystalline salts reporting 2-theta angles (deg) on the x axis while intensity (CPS) is reported on the y axis. In particular the spectra refers to compound 125 free base form I (A) and the following salts: tri-hydrochloride form I (B), L-malate form I (C), glycolate form I (D), malonate form I (E) salts.
Figure 2:
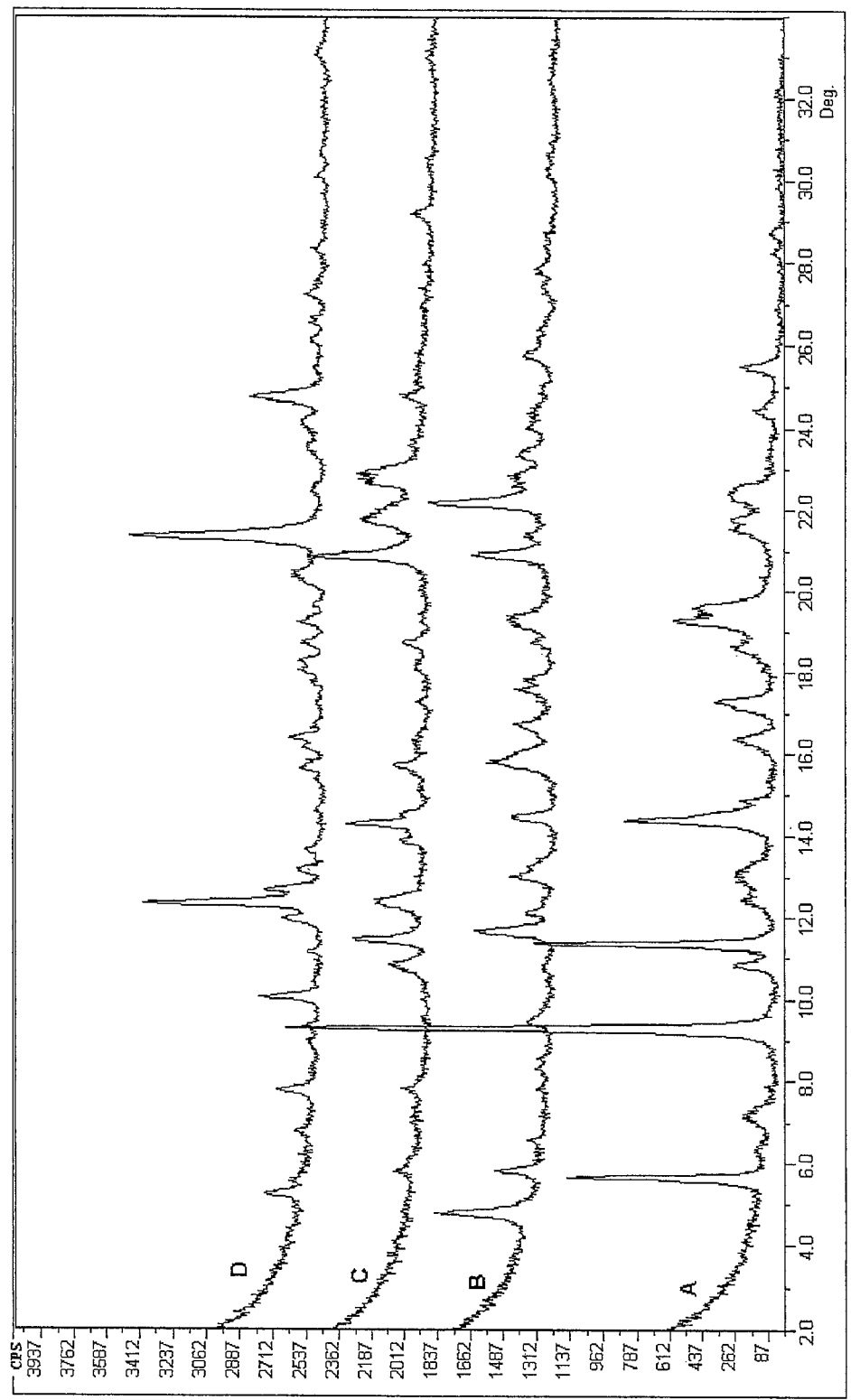
FIG. 2 shows the X-ray diffractograms of compound 125 free base form I (A) and the following salts: maleate form II (B), succinate form I (C), adipate form I (D) salts.
Figure 3:
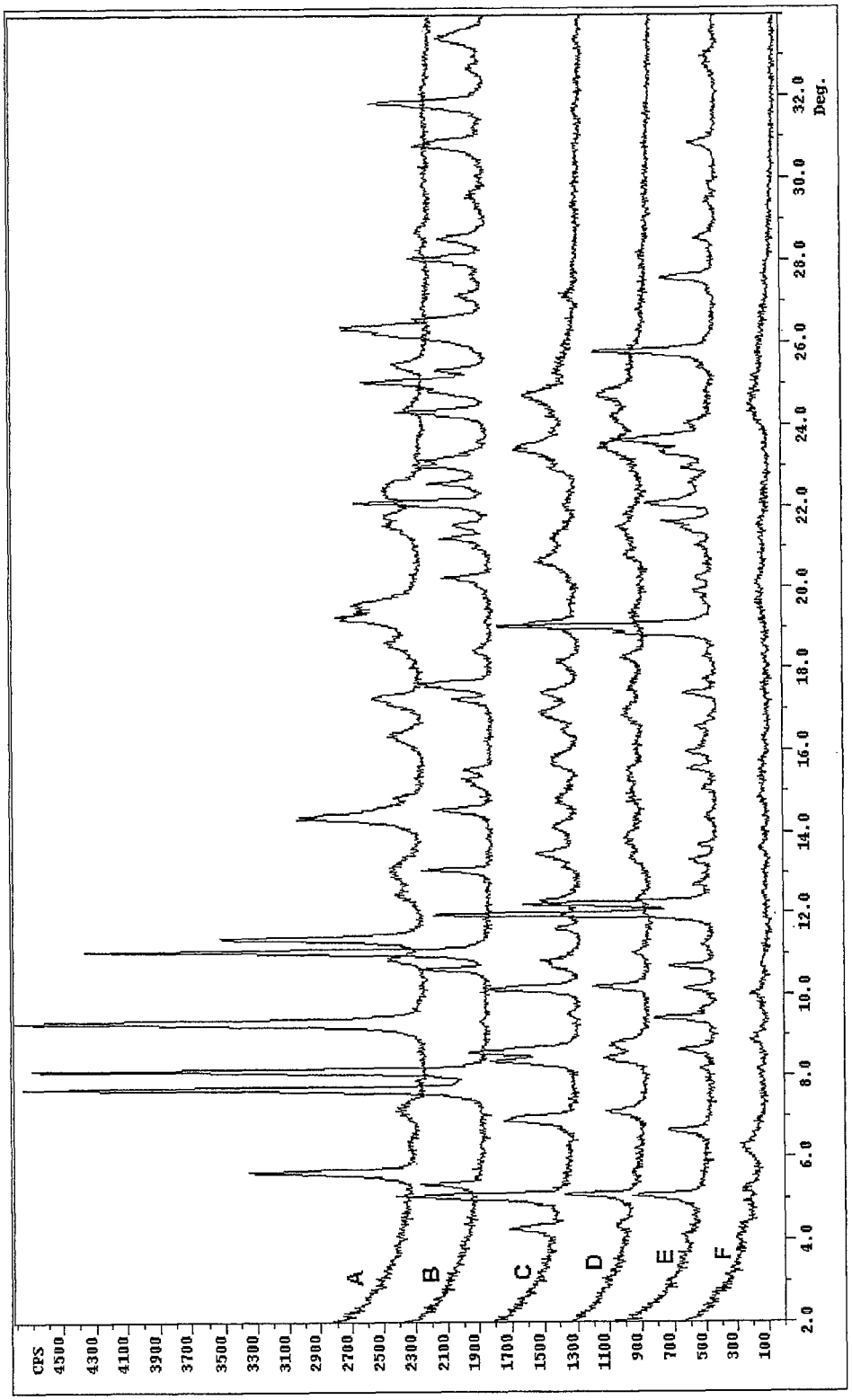
FIG. 3 shows the X-ray diffractograms of compound 125 free base form I (A) and the following salts: di-hydrochloride form I (B), L-lactate form I (C), mesylate form I (D), phosphate form I (E), fumarate semi-crystalline form I (F) salts.
Figure 4:
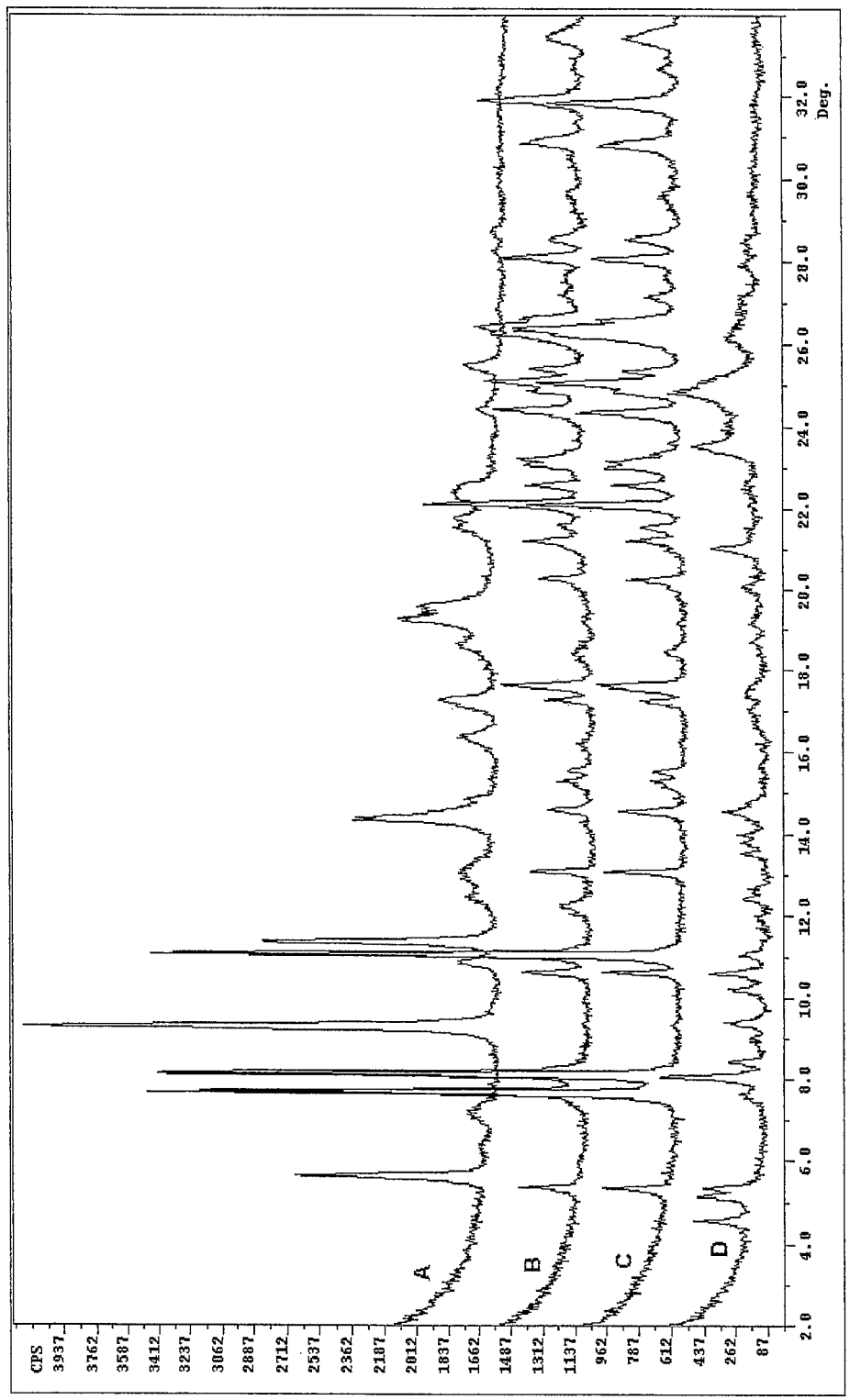
FIG. 4 shows the X-ray diffractograms of compound 125 free base form I (A) and the following salts: tri-hydrochloride form I (B), di-hydrochloride form I (C), hydrochloride form I (D) salts.

In a first aspect, the present invention relates to new salts and their crystal forms of compound 125 selected from fumarate, L-malate, maleate, succinate, adipate, malonate, glycolate, phosphate, mesylate and L-lactate salt.

In a further aspect, the present invention relates to new crystal forms of compound 125 selected from hydrochloride, di-hydrochloride and tri-hydrochloride salt.

These salts were found to be crystalline rendering these forms particularly suitable for pharmaceutical development.

Such salts of the compound 125 can be obtained by known analogy methods by means of the desired molar addition of solvent or aqueous solutions of the counterion to the free base dissolved in a suitable solvent. Such solvent is preferably an organic, in particular anhydrous, solvent chosen preferably from methanol, ethanol, dichloromethane and their mixtures. If necessary, the precipitation or the crystallization of the obtained salt may be favoured by addition or reworking in an anhydrous apolar solvent, for instance diethylether, n-hexane or cyclohexane.

According to the present invention, the definition of salts also comprises hydrates and polymorphs thereof. The present invention in particular relates to new crystalline forms and hydrates of the compound 125 maleate salt.

The term "hydrates" as used herein, means compounds formed by solvation, wherein the solvent is water. Then, in a further aspect, the present invention relates to stable crystal forms of the compound 125 as free base.

A further object of the invention is to provide a pharmaceutical composition comprising any salt of the compound 125 as above defined, a crystalline form or hydrate of the compound 125 maleate salt, or a crystal form of the compound 125 as free base as active ingredient and a pharmaceutically acceptable excipient and/or carrier.

A further object of the invention is to provide any salt of the compound 125 as above defined, a crystalline form or hydrate of the compound 125 maleate salt, or a crystal form of the compound 125 as free base for the use as a medicament, in particular as a CDK inhibitor.

A further object of the invention is to provide a method for treating a mammal, including a human being, in need of CDK inhibition comprising administering to said mammal a therapeutically effective amount of any salt of the compound 125 as above defined, a crystalline form or hydrate of the compound 125 maleate salt, or a crystal form of the compound 125 as free base.

Additionally, the present invention relates to any salt of the compound 125 as above defined, a crystalline form or hydrate of the compound 125 maleate salt, or a crystal form of the compound 125 as free base for use in a method of treating a mammal, comprising a human being, suffering from a disease state treatable by CDK inhibition, that means cell proliferative disorders such as cancer, viral infections, auto-immune diseases and neurodegenerative disorders.

Accordingly, any salt of the compound 125 as above defined, a crystalline form or hydrate of the compound 125 maleate salt, or a crystal form of the compound 125 as free base, either alone or in association with other therapeutic agents, is useful for treating a mammal, comprising humans, suffering from a disease state treatable by CDK inhibition, or in the preparation of a medicament for such treatment.

Therefore, the present invention also provides the use of any salt of the compound 125 as above defined, a crystalline form or hydrate of the compound 125 maleate salt, or a crystal form of the compound 125 as free base for the manufacture of a medicament for the treatment of a disease state treatable by CDK inhibition. The term "disease state treatable" means that the treatment according to the invention provides remission of the disease state or at least the conditions and quality of life of the mammal under treatment are improved. Examples of such disease states are in particular different cancers that may include all types of carcinomas, hematopoietic tumors of myeloid or lymphoid lineage, tumors of mesenchymal origin, tumors of the central and peripheral nervous system, melanoma, mesothelioma, seminoma, teratocarcinoma, osteosarcoma and Kaposi's sarcoma, but also cell proliferative diseases such as benign prostate hyperplasia, familial adenomatosis, polyposis, neuro-fibromatosis, psoriasis, vascular smooth cell proliferation associated with atherosclerosis, pulmonary fibrosis, arthritis, glomerulonephritis, post-surgical stenosis and restenosis, organ transplant rejection and host versus graft disease.

The effective dose of compound 125 salts may vary according to the disease, severity of the disorder and the conditions of the patient to be treated. Therefore the physician, as always, must set the optimal dose for each patient. Anyway, the effective dosage range may be from about 20 mg/day to about 300 mg/day, preferably from about 50 mg/day to about 150 mg/day (calculated as free base), either as a single or multiple divided daily dosages.

A salt of the compound 125 as above defined, a crystalline form or hydrate of the compound 125 maleate salt, or a crystal form of the compound 125 as free base, is readily orally absorbed, therefore it is preferably orally administered.

Needless to say, the compounds of the present invention may be administered by any administration route, for instance by parenteral, topical, rectal and nasal route.

Hence, in a first aspect, the present invention relates to fumarate, L-malate, maleate, succinate, adipate, malonate, glycolate, phosphate, mesylate and L-lactate salts of the compound 125.

The preferred salts of the present invention are L-malate, maleate, malonate, glycolate, phosphate and L-lactate salts of the compound 125.

More preferred salts of the compound 125 are maleate, malonate and glycolate.

As stated above, the present invention also relates to new crystalline forms and hydrates of compound 125 salts.

In another aspect, the present invention relates to new crystalline forms of compound 125 as free base.

As a further aspect it has been found that compound 125 maleate salt can be obtained as a crystalline solid in three different crystal forms named Form I, Form II and Form III.

Form I is a high melting crystal form of compound 125 maleate salt that is characterized as a hydrated form that shows reversible adsorption of about 1 mole of water at room conditions (e.g. 25° C./60% RH) and undergoes conversion to form III by effect of exposition to stressed conditions of temperature and/or humidity (e.g. storage at 40° C./75% RH).

The total uptake of about 3.0±3.5% at 25° C. and 90% relative humidity (RH) is reversible by lowering RH at about 20% at the same temperature.

Form II is a high melting crystal form of compound 125 showing the property of retaining non-stoichiometric amounts of solvents in the crystal lattice (e.g. alcohols such as ethanol, butanol, propanol) and undergoes conversion to form I or III by effect of drying conditions or exposition to stressed conditions of temperature and humidity (e.g. storage at 40° C./75% RH).

Form III is a high melting crystal form of compound 125 maleate salt that is characterized as a hydrated form that shows reversible adsorption of about 1 mole of water at room conditions (e.g. 25° C./60% RH). The uptake of about 3.0±3.5% at 25° C. and 90% relative humidity (RH) is reversible by lowering RH at about 20% at the same temperature.

As a further aspect it has been found that compound 125 maleate salt can be obtained as a crystalline solid in molar ratios of 0.5:1, 1:1 and 2:1.

Compound 125 glycolate salt and compound 125 malonate salt are slightly hygroscopic, both showing a reversible water upatake of about 2.5% at 25° C./90% RH.

Compound 125 salts show good solubility, in particular the solubility of the maleate, malonate, glycolate salts in 0.5% dextrose solution is about 10 mg/ml or higher.

Besides the advantage of exhibiting high water solubility, the compound 125 salts, in particular maleate, malonate, glycolate salts, are also particularly suitable to be manufactured reproducibly in a clear acid/base ratio.

This finding renders these salts particularly suitable for the use in liquid formulations for oral as well as for intravenous formulations.

TABLE 1

Description of the solid state properties of the salts and free base forms of compound 125.

| Compound 125 Salt (*) | Crystal Form | PXRD FIG. | PXRD Table | Significant PXRD peaks (2-theta, deg) (**) | DSC FIG. |
|---|---|---|---|---|---|
| Maleate | I | 11 | 7 | 5.3, 6.0, 11.9, 12.7, 13.5, 14.5, 17.9, 19.4, 20.9, 22.9, 23.2, 24.7 | 20 |
| Maleate | II | 2B, 12 | 8 | 4.8, 9.6, 11.6, 15.7, 16.0, 16.7, 19.3, 20.9, 21.3, 22.1, 23.3, 27.7, | 17F |
| Maleate | III | 5D, 13 | 9 | 6.0, 11.8, 12.3, 13.3, 14.3, 16.3, 17.8, 20.8, 22.8, 24.3, 26.4, 27.6 | 20 |
| Malonate | I | 1E, 7 | 3 | 11.5, 12.4, 14.3, 15.8, 18.8, 20.9, 21.8, 22.7, 23.0, 24.8 | 16B |
| Glycolate | I | 1D, 6 | 2 | 6.6, 11.8, 12.2, 12.7, 16.1, 17.5, 19.4, 21.9, 23.6, 23.9, 25.9, 27.8 | 17B |
| Tri-Hydrochloride | I | 1B, 4B, 8 | 4 | 7.7, 8.2, 10.6, 11.1, 17.6, 22.1, 23.2, 24.4, 25.1, 26.4, 28.1, 31.9 | 18A |
| Di-Hydrochloride | I | 4C, 9 | 5 | 7.7, 8.1, 11.0, 22.1, 26.4, 25.1, 31.8, 24.3, 28.1, 10.6, 17.6, 23.0 | 18B |

TABLE 1-continued

Description of the solid state properties of the salts and free base forms of compound 125.

| Compound 125 Salt (*) | Crystal Form | PXRD FIG. | PXRD Table | Significant PXRD peaks (2-theta, deg) (**) | DSC FIG. |
|---|---|---|---|---|---|
| Hydrochloride | I | 4D, 10 | 6 | 4.6, 5.2, 5.4, 8.1, 8.4, 9.4, 10.2, 10.6, 14.6, 21.0, 23.5, 24.9 | 18C |
| Freebase | I | 1A, 2A, 3A, 4A, 14 | 10 | 5.6, 9.3, 10.9, 11.4, 14.4, 14.5, 17.3, 19.3, 19.6, 21.8, 22.4, 25.5 | 16A, 17A |
| Freebase | II | 15 | 11 | 6.1, 10.3, 11.4, 11.9, 12.6, 14.5, 18.5, 18.9, 20.3, 23.0, 24.8, 25.7 | Not available |

Note (*):
if not differently specified, the described salts are intended in the 1:1 molar ratio between freebase and counterion.

Note (**):
the reported PXRD peaks have been selected according their higher intensity among the complete dataset.

Figure 11:
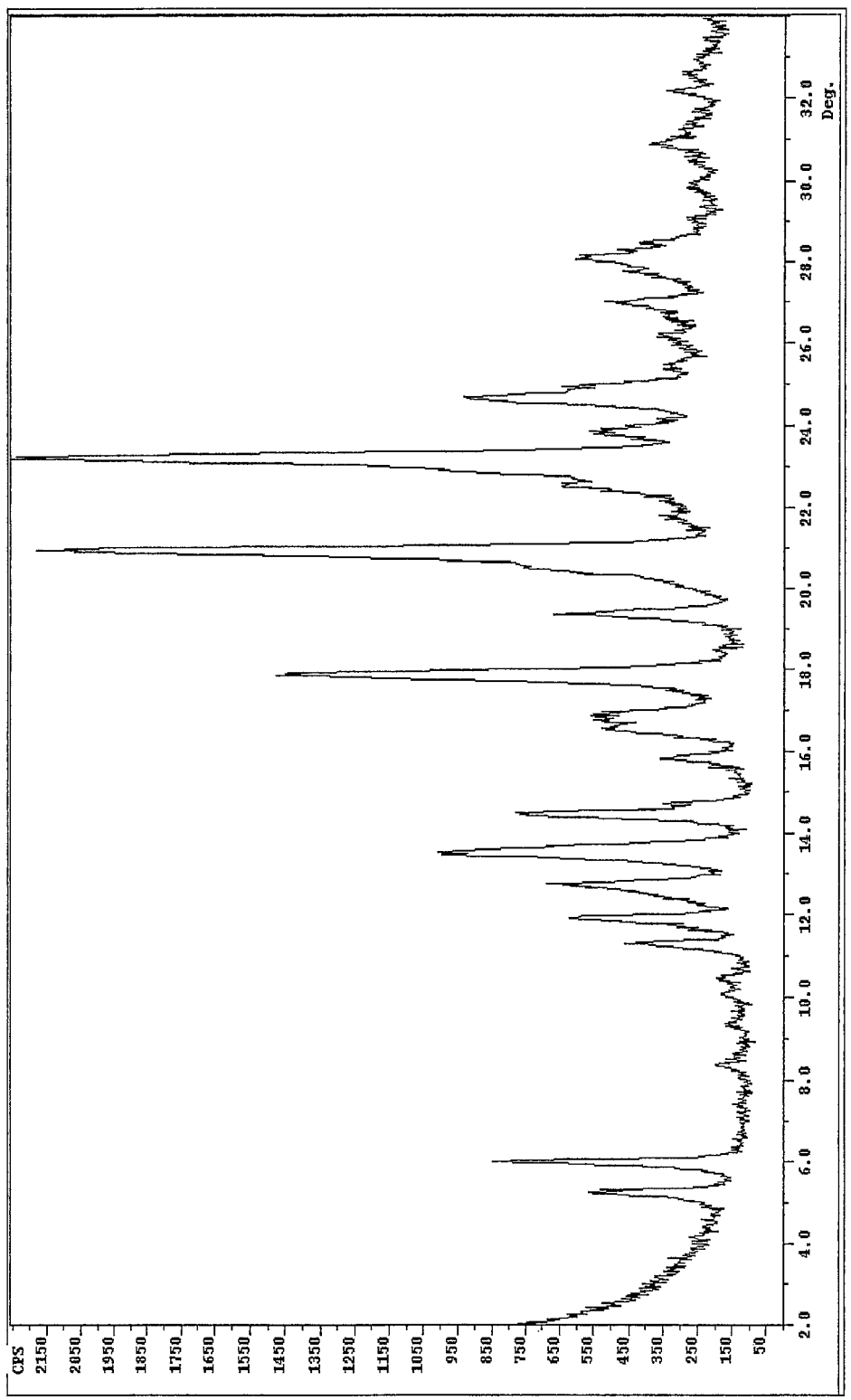
FIG. 11 shows the X-ray diffractogram of compound 125 maleate salt, form in I in the 1:1 molar ratio between freebase and counterion.

In a preferred embodiment, the form I of the essentially pure maleate salt of compound 125 in the 1:1 molar ratio between freebase and counterion, shows the X-ray diffraction diagram indicated in FIG. 11.

High preference is also given for the form I of the maleate salt of compound 125 in the 1:1 molar ratio between freebase and counterion, which shows an X-ray diffraction diagram of the type shown in FIG. 11, with significant peak intensities at about the 2-theta values (deg) described in table 1.

In samples being free of any additional materials (other crystal forms, excipients), it should be possible to observe diffraction peaks at about the 2-theta values (deg) described in table 7.

Figure 12:
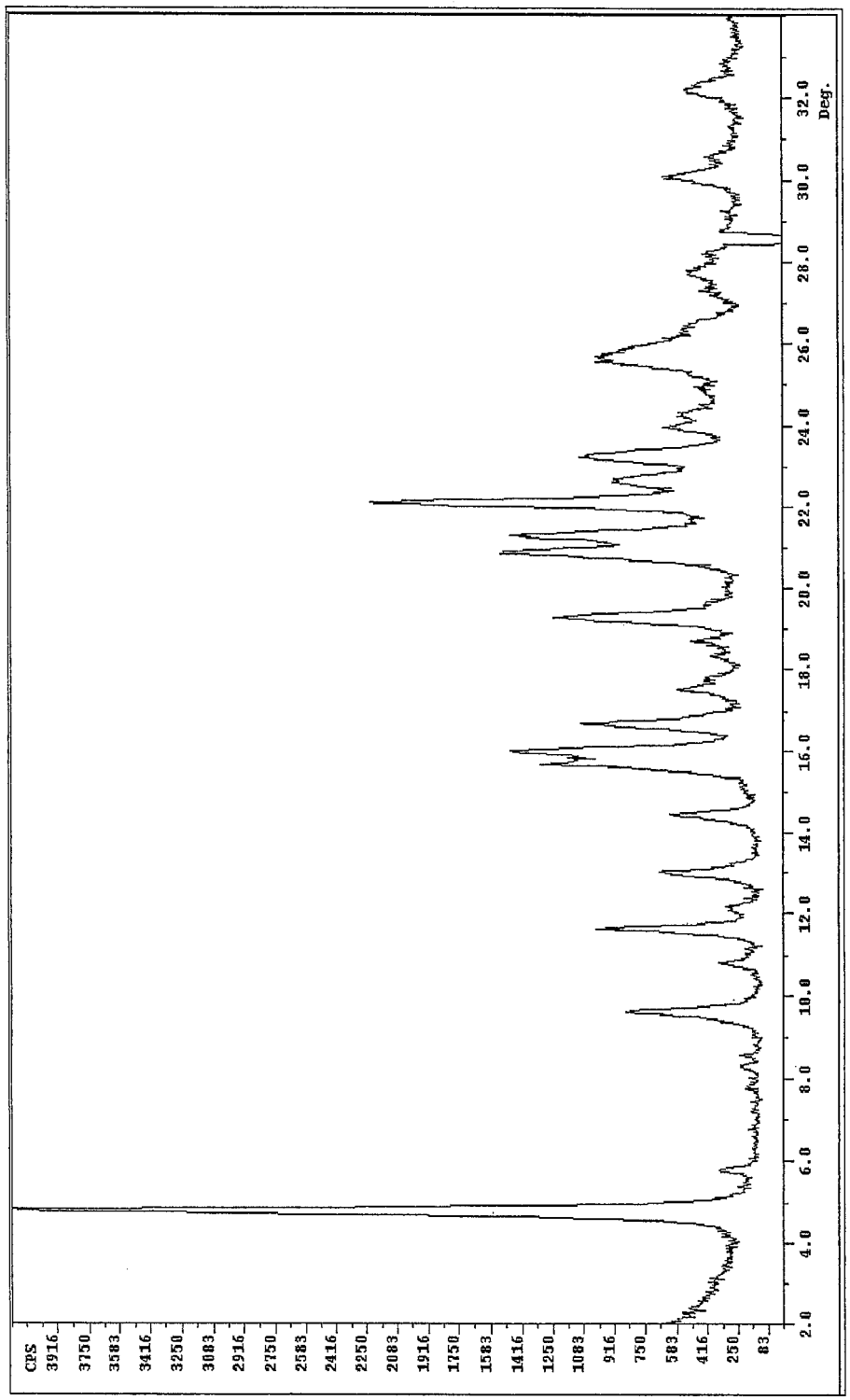
FIG. 12 shows the X-ray diffractogram of compound 125 maleate salt, form II in the 1:1 molar ratio between freebase and counterion.

In another preferred embodiment, the form II of the essentially pure maleate salt of compound 125 in the 1:1 molar ratio between freebase and counterion, shows the X-ray diffraction diagram indicated in FIG. 12.

High preference is also given for the form II of the maleate salt of compound 125 in the 1:1 molar ratio between freebase and counterion, which shows an X-ray diffraction diagram of the type shown in FIG. 12, with peak intensities at the 2-theta values (deg) described in table 1.

In samples being free of any additional materials (other crystal forms, excipients), it should be possible to observe diffraction peaks at about the 2-theta values described in table 8.

Figure 13:
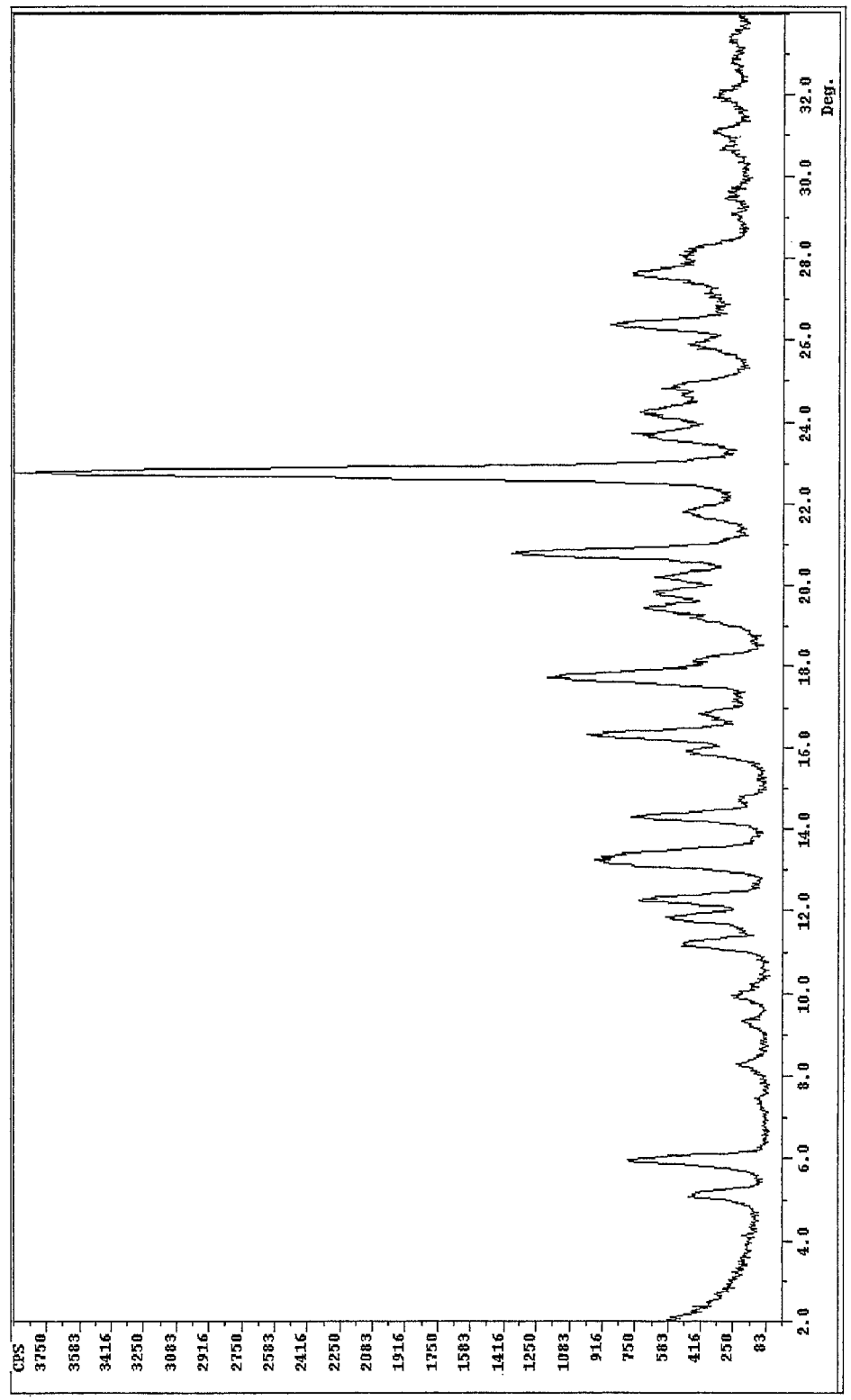
FIG. 13 shows the X-ray diffractogram of compound 125 maleate salt, form III in the 1:1 molar ratio between freebase and counterion.

In another preferred embodiment, the form III of the essentially pure maleate salt of compound 125 in the 1:1 molar ratio between freebase and counterion, shows the X-ray diffraction diagram indicated in FIG. 13.

High preference is also given for the form III of the maleate salt of compound 125 in the 1:1 molar ratio between freebase and counterion, which shows an X-ray diffraction diagram of the type shown in FIG. 13, with peak intensities at the 2-theta values (deg) described in table 1.

In samples being free of any additional materials (other crystal forms, excipients), it should be possible to observe diffraction peaks at about the 2-theta values (deg) described in table 9.

Figure 6:
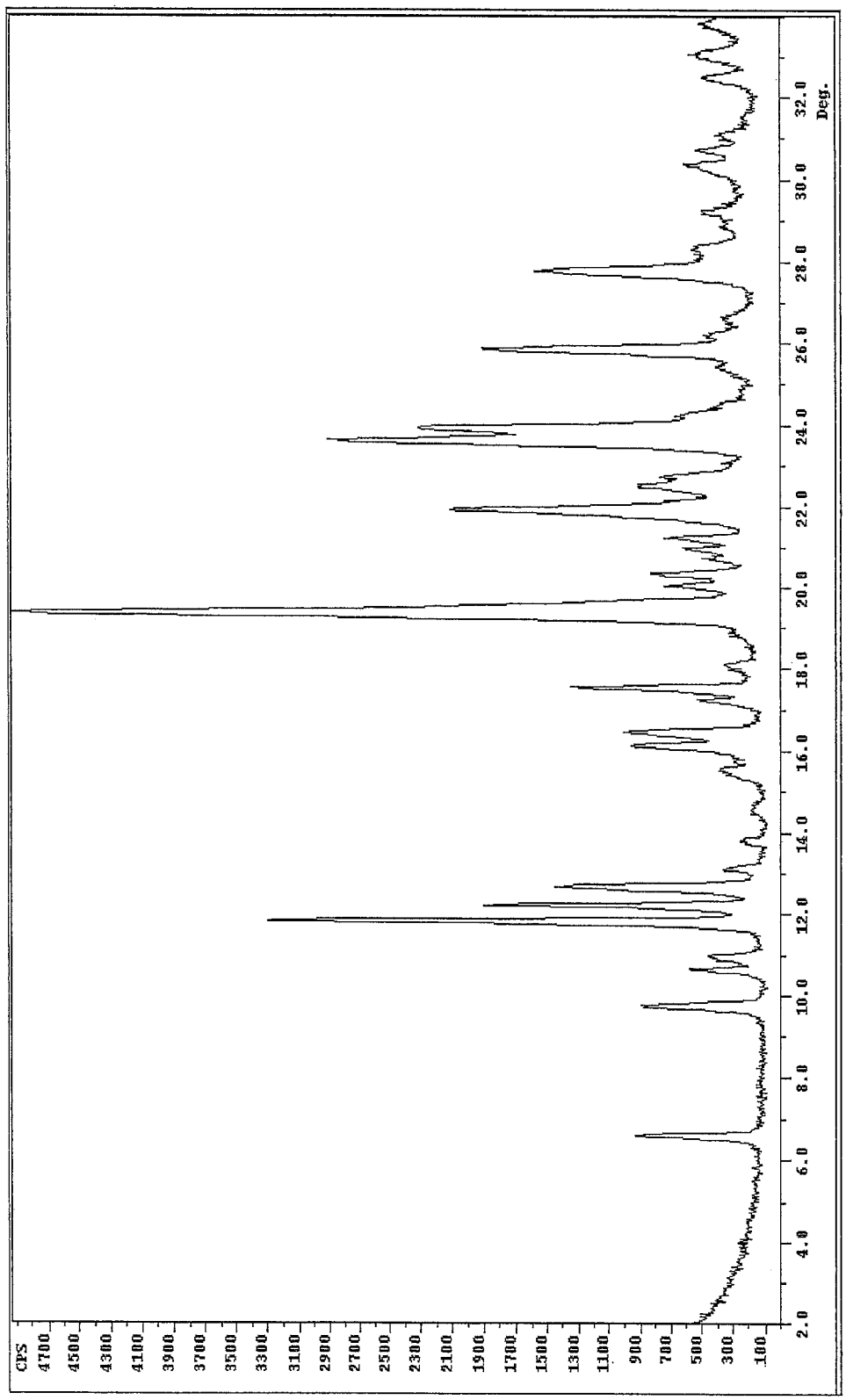
FIG. 6 shows the X-ray diffractogram of compound 125 glycolate salt, form I.

In another preferred embodiment, the form I of the essentially pure glycolate salt of compound 125 shows in the 1:1 molar ratio between freebase and counterion, the X-ray diffraction diagram indicated in FIG. 6.

High preference is also given for the form I of the glycolate salt of compound 125 in the 1:1 molar ratio between freebase and counterion, which shows an X-ray diffraction diagram of the type shown in FIG. 6, with peak intensities at the 2-theta values (deg) described in table 1.

In samples being free of any additional materials (other crystal forms, excipients), it should be possible to observe diffraction peaks at about the 2-theta values (deg) described in table 2.

Figure 7:
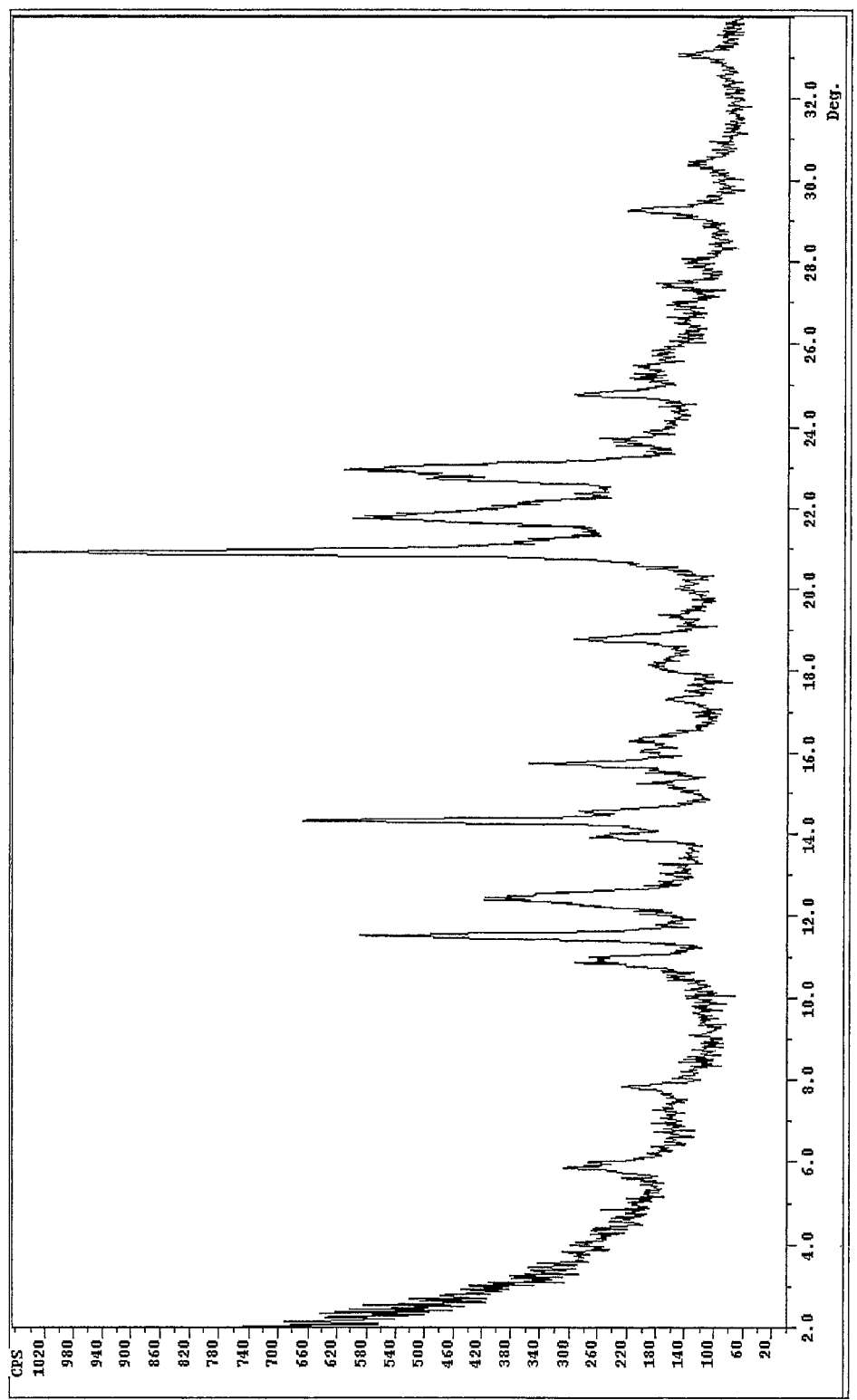
FIG. 7 shows the X-ray diffractogram of compound 125 malonate salt, form I.

In another preferred embodiment, the form I of the essentially pure malonate salt of compound 125 in the 1:1 molar ratio between freebase and counterion, shows the X-ray diffraction diagram indicated in FIG. 7.

High preference is also given for the form I of the malonate salt of compound 125 in the 1:1 molar ratio between freebase and counterion, which shows an X-ray diffraction diagram of the type shown in FIG. 7, with peak intensities at the 2-theta values (deg) described in table 1.

In samples being free of any additional materials (other crystal forms, excipients), it should be possible to observe diffraction peaks at about the 2-theta values (deg) described in table 3.

Figure 8:
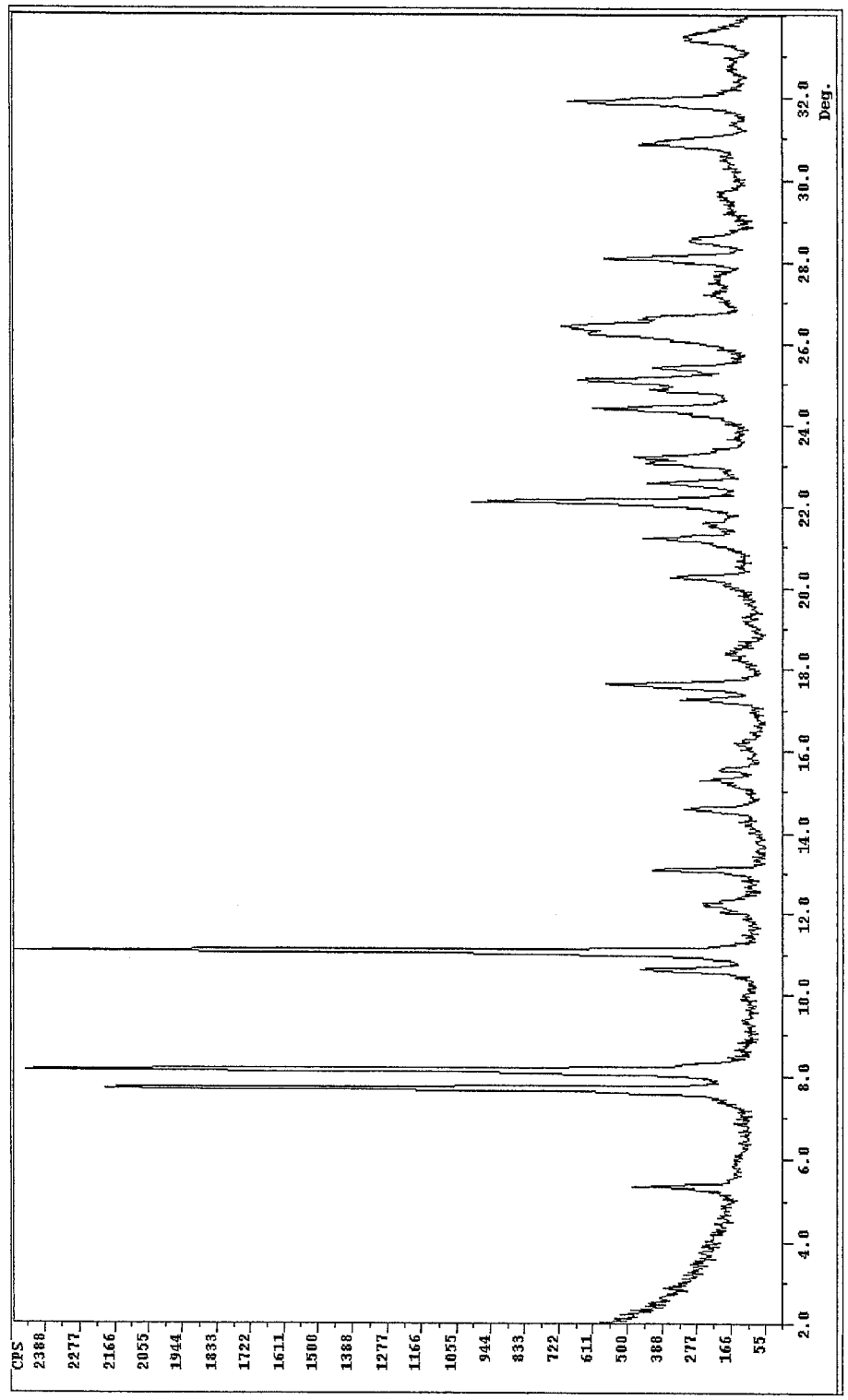
FIG. 8 shows the X-ray diffractogram of compound 125 tri-hydrochloride salt, form I.

In another preferred embodiment, the form I of the essentially pure tri-hydrochloride salt of compound 125 shows the X-ray diffraction diagram indicated in FIG. 8.

High preference is also given for the form I of the tri-hydrochloride salt of compound 125 which shows an X-ray diffraction diagram of the type shown in FIG. 8, with peak intensities at the 2-theta values (deg) described in table 1.

In samples being free of any additional materials (other crystal forms, excipients), it should be possible to observe diffraction peaks at about the 2-theta values (deg) described in table 4.

Figure 9:
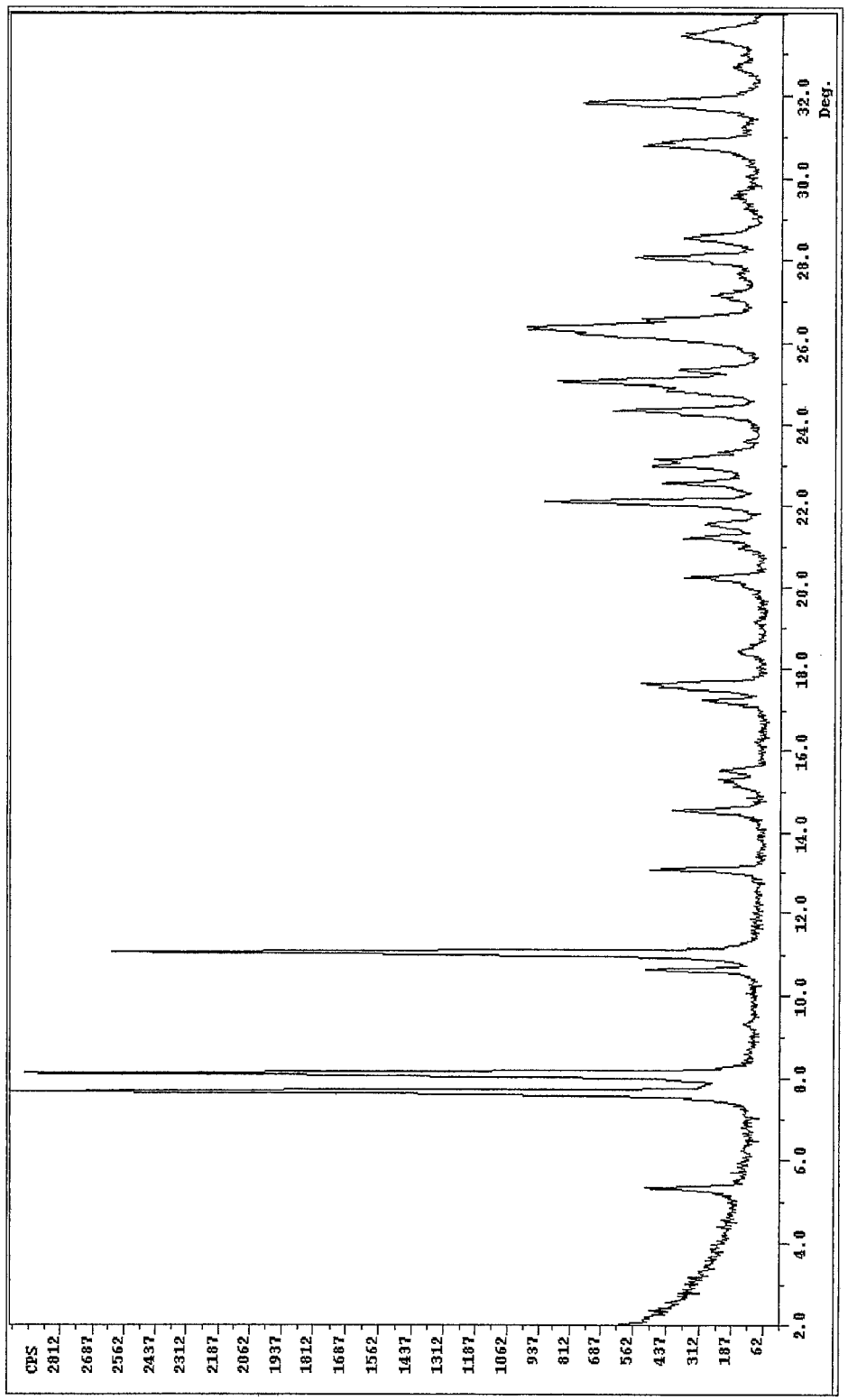
FIG. 9 shows the X-ray diffractogram of compound 125 di-hydrochloride salt, form I.

In another preferred embodiment, the form I of the essentially pure di-hydrochloride salt of compound 125 shows the X-ray diffraction diagram indicated in FIG. 9.

High preference is also given for the form I of the di-hydrochloride salt of compound 125 which shows an X-ray diffraction diagram of the type shown in FIG. 9, with peak intensities at the 2-theta values (deg) described in table 1.

In samples being free of any additional materials (other crystal forms, excipients), it should be possible to observe diffraction peaks at about the 2-theta values (deg) described in table 5 below.

Figure 10:
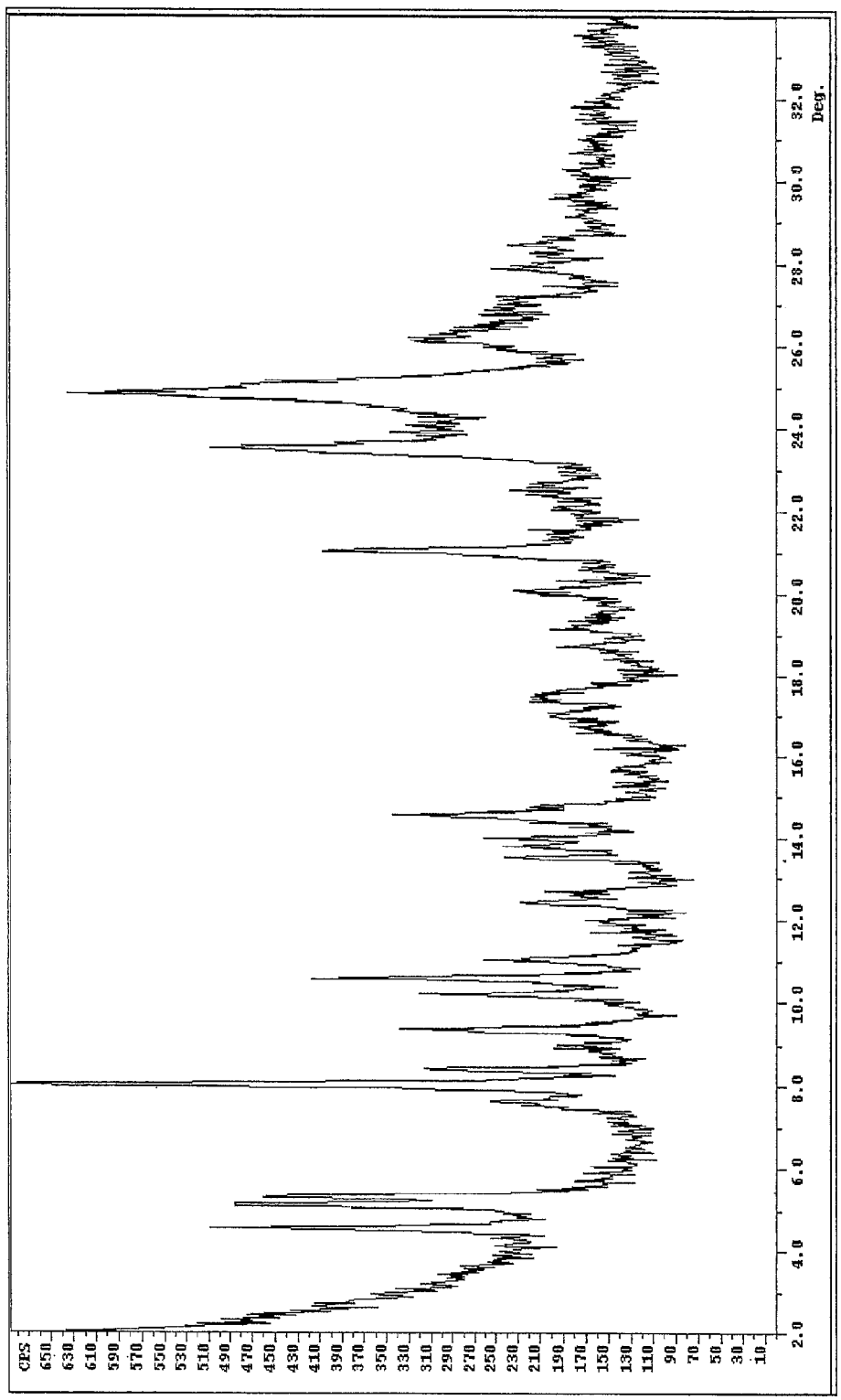
FIG. 10 shows the X-ray diffractogram of compound 125 hydrochloride salt, form I.

In another preferred embodiment, the form I of the essentially pure hydrochloride salt of compound 125 shows the X-ray diffraction diagram indicated in FIG. 10.

High preference is also given for the form I of the hydrochloride salt of compound 125 which shows an X-ray diffraction diagram of the type shown in FIG. 10, with peak intensities at the 2-theta values (deg) described in table 1.

In samples being free of any additional materials (other crystal forms, excipients), it should be possible to observe diffraction peaks at about the 2-theta values (deg) described in table 6 below.

Figure 14:
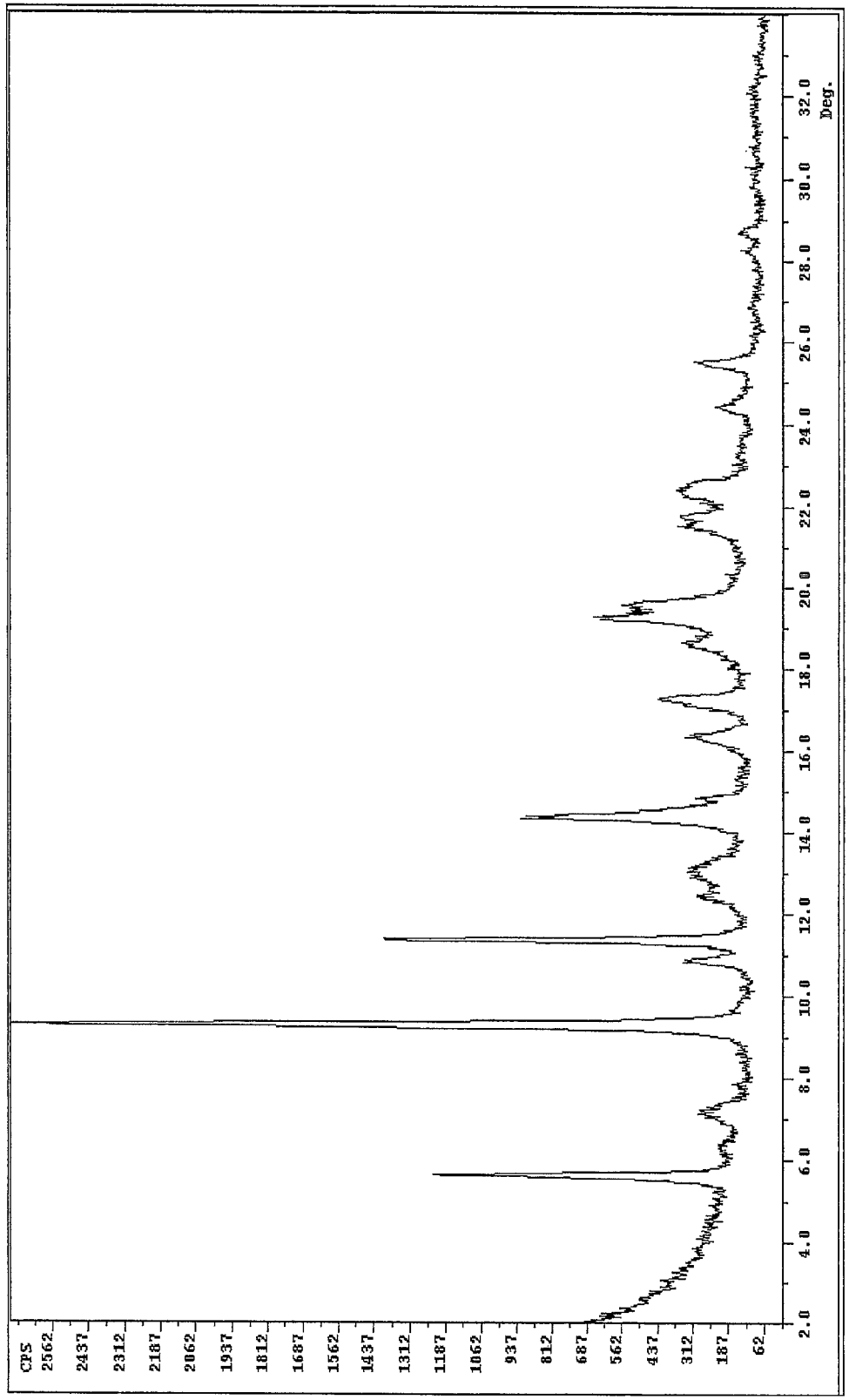
FIG. 14 shows the X-ray diffractogram of compound 125 free base, form I.

In another preferred embodiment, the form I of the essentially pure compound 125 free base shows the X-ray diffraction diagram indicated in FIG. 14.

High preference is also given for the form I of the compound 125 free base which shows an X-ray diffraction diagram of the type shown in FIG. 14, with peak intensities at the 2-theta values (deg) described in table 1.

In samples being free of any additional materials (other crystal forms, excipients), it should be possible to observe diffraction peaks at about the 2-theta values (deg) described in table 10 below.

Figure 15:
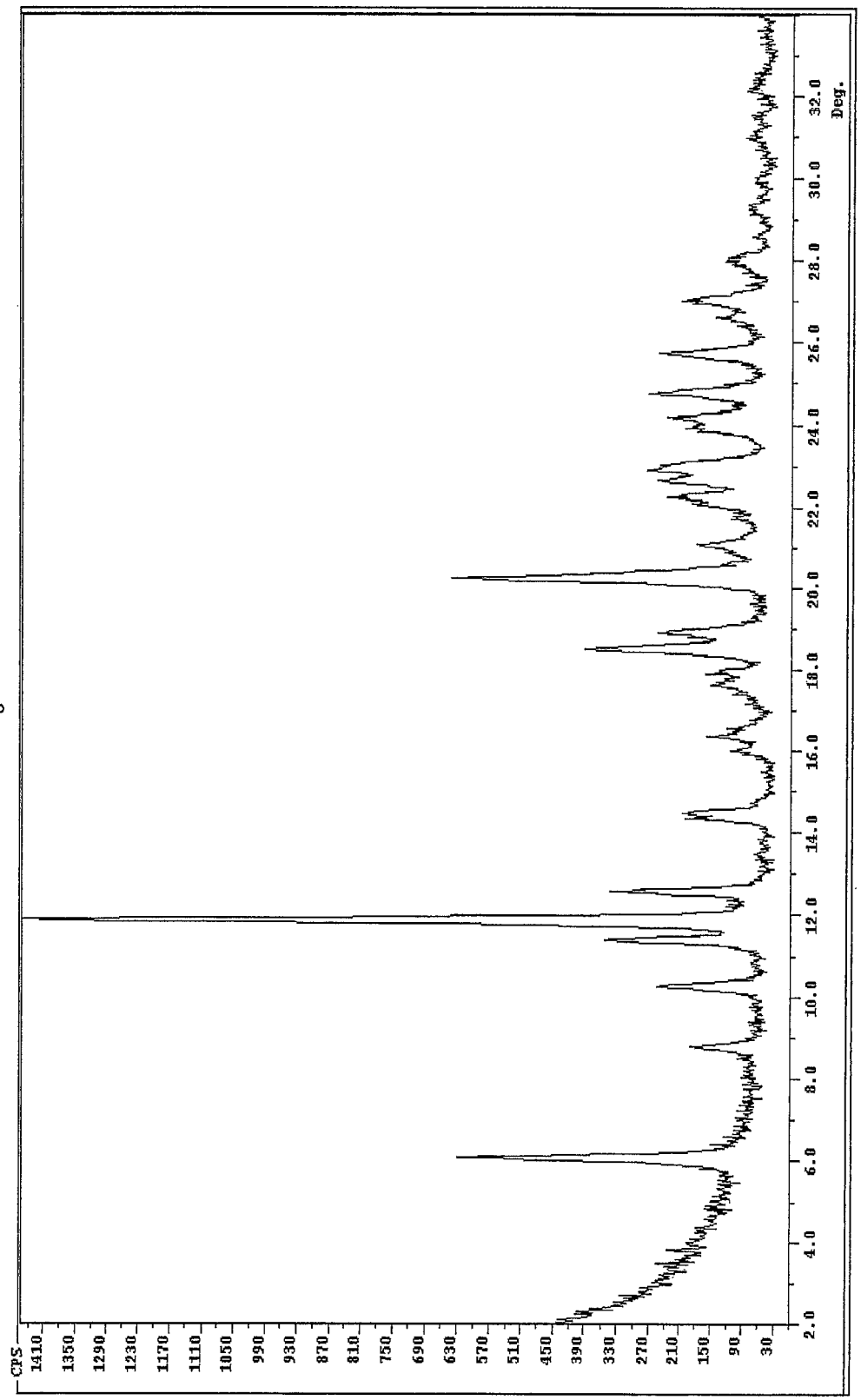
FIG. 15 shows the X-ray diffractogram of compound 125 free base, form II obtained by means of precipitation of a salt of compound 125 dissolved in buffer solution at pH 6.8.

In another preferred embodiment, the form II of the essentially pure compound 125 free base shows the X-ray diffraction diagram indicated in FIG. 15.

High preference is also given for the form I of the compound 125 free base which shows an X-ray diffraction diagram of the type shown in FIG. 15, with peak intensities at the 2-theta values (deg) described in table 1. In samples being free of any additional materials (other crystal forms, excipients), it should be possible to observe diffraction peaks at about the 2-theta values (deg) described in table 11 below.

As a further aspect it has been found that compound 125 maleate salt can be obtained as a crystalline solid in molar ratio of 0.5:1 between freebase and counterion.

Figure 5:
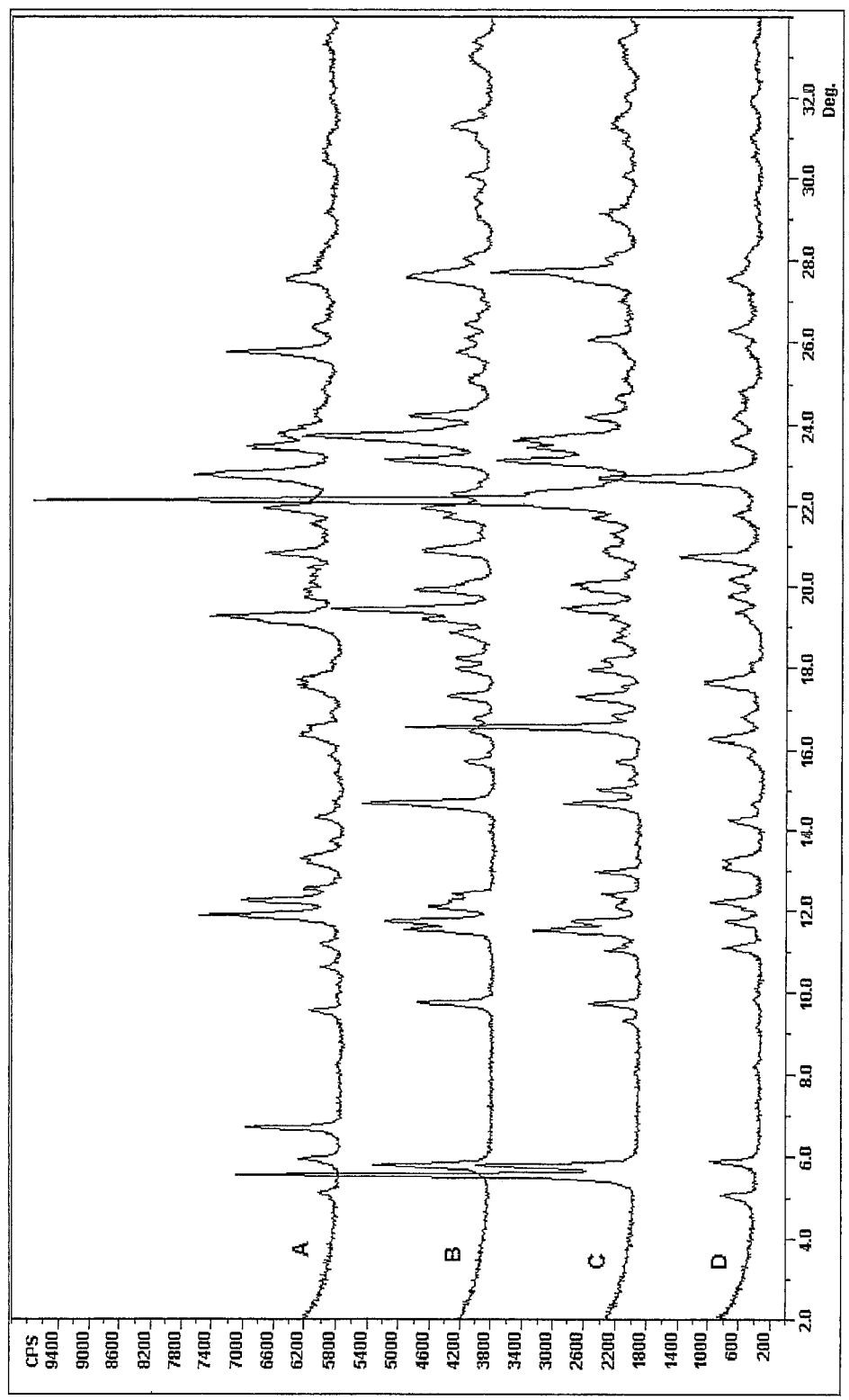
FIG. 5 shows the X-ray diffractogram of compound 125 maleate salt form I (A) in the 0.5:1 molar ratio between freebase and counterion, compound 125 maleate salt form II (B) in the 2:1 molar ratio between freebase and counterion, compound 125 maleate salt form I (C) in the 2:1 molar ratio between freebase and counterion, and compound 125 maleate salt, form III (D) in the 1:1 molar ratio between freebase and counterion.

In another preferred embodiment, the form I of the essentially pure maleate salt of compound 125 in the 0.5:1 molar ratio between freebase and counterion, shows the X-ray diffraction diagram coded A in FIG. 5.

As a further aspect it has been found that compound 125 maleate salt can be obtained as a crystalline solid in molar ratio of 2:1 between freebase and counterion.

High preference is also given for the form I of the essentially pure maleate salt of compound 125 in the 2:1 molar ratio between freebase and counterion, that shows the X-ray diffraction diagram coded C in FIG. 5.

In another preferred embodiment, the form II of the essentially pure maleate salt of compound 125 in the 2:1 molar ratio between freebase and counterion, shows the X-ray diffraction diagram coded B in FIG. 5.

Essentially pure means that the crystal forms of the present invention have a purity of at least 90%. More preferably the crystal forms of the present invention have a purity of at least 95%, and most preferably at least 99% by weight of the crystals of an acid addition salt or free base of compound 125 are present in the crystal form according to the invention.

As a further aspect concerning solid state characterization by means of DSC, it has been found that compound 125 succinate, L-lactate, adipate, phosphate, mesylate, fumarate and L-malate salts, characterized as crystalline materials by means of PXRD, show complex DSC profile. Such salts undergo thermal transitions involving desolvation/dehydration processes and subsequent melting of desolved/dehydrated forms characterized by their DSC melting peak temperatures. Further thermal transitions may follow when e.g. degradation occurs.

As a further aspect concerning solid state characterization by means of DSC, it has been found that compound 125 tri-hydrochloride, di-hydrochloride and hydrochloride also show complex DSC profile. Such salts undergo thermal transitions involving desolvation/dehydration processes and subsequent features related to melting with degradation and loss of HCl characterized by their DSC melting peak temperatures.

As a further aspect concerning solid state characterization by means of DSC, it has been found that compound 125 malonate salt also shows complex DSC profile. This salt undergo thermal transitions involving melting and subsequent degradation and vaporization of the counterion probably followed by crystallization of the free base and its subsequent melting, those features being characterized by their DSC melting peak temperatures.

It will be understood that the onset and/or peak temperature values of the DSC may vary slightly from one machine to another, one method to another or from one sample to another, and so the values quoted are not to be construed as absolute. In fact, observed temperatures will depend on the rate of temperature change as well as sample preparation technique and the particular instrument employed. It will be estimated and taken into account that the temperature values obtained applying such different conditions may vary by plus or minus about 4° C. Results are further described in table I and example 6.

According to a further aspect of the invention a pharmaceutical composition can be formulated according to known method in the art in any of the pharmaceutical forms known in the art for administration to a mammal, including humans.

For instance, a pharmaceutical composition which comprises a salt of compound 125, as defined herein in association with a pharmaceutically acceptable diluent or carrier. The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or as a suppository for rectal dosing.

The compositions of the invention may be obtained by conventional procedures using conventional pharmaceutical excipients, well known in the art.

Thus, compositions intended for oral use may contain, for example, one or more colouring, sweetening, flavouring and/or preservative agents.

Suitable pharmaceutically acceptable excipients for a tablet formulation include, for example, fillers such as lactose, mannitol, microcrystalline cellulose, sodium carbonate, pregelatinized starch, calcium phosphate or calcium carbonate; granulating and disintegrating agents such as sodium croscarmellose, corn starch, crospovidone or sodium starch glycolate; binding agents such as starch, microcrystalline cellulose, povidone, sucrose; lubricating agents such as magnesium stearate, stearic acid, sodium stearyl fumarate, polyethylene glycols or talc; glidants, such as colloidal silicon dioxide; preservative agents such as ethyl or propyl p-hydroxybenzoate, and anti-oxidants, such as ascorbic acid.

Tablet formulations may be uncoated or coated either to modify their disintegration and the subsequent absorption of the active ingredient within the gastrointestinal track, or to improve their stability and/or appearance, in either case, using conventional coating agents and procedures well known in the art. Compositions for oral use may be in the form of hard gelatin capsules in which the active ingredient is mixed with an inert solid diluent, for example, calcium carbonate, calcium phosphate or kaolin and including the above mentioned excipients for tablet formulations, or as soft gelatin capsules in which the active ingredient is mixed with water or an oil such as peanut oil, liquid paraffin, soya bean oil, coconut oil, or preferably olive oil, or any other acceptable vehicle. Compositions for oral use may also be in the form of hard gelatin capsules in which the active ingredient is formulated as a stable pharmaceutical solid or semisolid dispersion comprising the active ingredient and, for example, a hydrophilic carrier, a water-soluble vitamin E derivative as antioxidant agent and optionally other excipients. Aqueous suspensions generally contain the active ingredient in finely powdered form together with one or more suspending agents, such as sodium carboxymethylcellulose, methylcellulose, hydroxypropylmethylcellulose, sodium alginate, polyvinylpyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate.

The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame). Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol.

Sweetening agents such as those set out above, and flavouring agents may be added to provide a palatable oral preparation.

These compositions may be preserved by the addition of an anti-oxidant such as ascorbic acid.

Dispersible or lyophilised powders and granules suitable for preparation of an aqueous suspension or solution by the addition of water generally contain the active ingredient together with a dispersing or wetting agent, suspending agent and one or more preservatives.

Suitable dispersing or wetting agents and suspending agents are exemplified by those already mentioned above.

Additional excipients such as sweetening, flavouring and colouring agents, may also be present.

The pharmaceutical compositions of the invention may also be in the form of oil-in-water emulsions.

The oily phase may be a vegetable oil, such as olive oil or arachis oil or a mineral oil, such as for example liquid paraffin or a mixture of any of these.

Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate.

The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent. The pharmaceutical compositions may also be in the form of a sterile injectable aqueous or oily suspension, solutions, emulsions or particular systems, which may be formulated according to known procedures using one or more of the appropriate dispersing or wetting agents and suspending agents, which have been mentioned above.

A sterile injectable preparation may also be a sterile injectable solution or suspension in a non-toxic parenterally-acceptable diluent or solvent, for example a solution in polyethylene glycol.

Suppository formulations may be prepared by mixing the active ingredient with a suitable non-irritating excipient which is solid at ordinary temperatures but liquid at the rectal temperature and will therefore melt in the rectum to release the drug.

Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30 µm or much less preferably 5 µm or less and more preferably between µm and 1 µm, the powder itself comprising either active ingredient alone or diluted with one or more physiologically acceptable carriers such as lactose.

The powder for insufflation is then conveniently retained in a capsule containing, for example, 1 to 50 mg of active ingredient for use with a turbo-inhaler device. Compositions for administration by inhalation may be in the form of a conventional pressurised aerosol arranged to dispense the active ingredient either as an aerosol containing finely divided solid or liquid droplets.

Conventional aerosol propellants such as volatile fluorinated hydrocarbons or hydrocarbons may be used and the aerosol device is conveniently arranged to dispense a metered quantity of active ingredient. Examples of compositions for oral use in the form of hard gelatin capsules are described in example 10.

EXAMPLES

The following Examples illustrate the invention.
Temperatures are measured in degrees Celsius (° C.).
Unless otherwise indicated, the reactions or experiments take place at room temperature.
Abbreviations:
RT: room temperature
RH: relative humidity
PXRD: powder X-ray diffraction
DSC: Differential Scanning Calorimetry
DVS: Dynamic Vapor Sorption
TGA: Thermogravimetric Analysis Example 1

Compound 125 Salt Formation Experiments

An aliquot of compound 125 (about 500 mg) was dissolved at RT in 10 mL of a 1:1 mixture of Methanol and Dichloromethane, obtaining a nominal concentration of about 50 mg/mL.

Several experiments of salt formation were then performed by addition of 1:1 molar amounts of the counterions to 0.7 mL of the described compound 125 free base solution at RT.

Cooling crystallization experiments at −30° C. were performed with resting times of about 24-36 h.

The obtained precipitates were collected by vacuum filtration and dried at 40° C. under vacuum.

When crystallization did not occur, the solutions were concentrated by evaporated at RT under a mild nitrogen flow to allow precipitation.

In some cases, a further step of re-crystallization (e.g. compound triturated in diethylether) was required to isolate a crystalline or at least powdery sample starting from a gluey residue.

Drying was allowed at 40° C. under vacuum conditions.

Chemical identification of compound 125 and acidic counterion was performed by ¹H NMR (described in example 9).

Example 2

Gram-Scale Preparation of Compound 125 Glycolate, Maleate and Malonate Salts

The free base was dissolved at reflux in absolute ethanol when preparing glycolate and maleate salts while methanol was used to prepare malonate salt at reflux conditions as well.

1 equivalent of the acidic counterion was added after complete dissolution of the free base.

After an appropriate duration of reflux working in the reaction vessel, the heating was interrupted to achieve spontaneous cooling down to RT. This phase allowed precipitation of glycolate salt while maleate and malonate salts respectively required a further cooling step down to 0° C. and −20° C. The precipitated materials were then filtered and dried for at least 24 hrs at 40° C. under vacuum.

Example 3

Scaled Up Preparation of Compound 125 Maleate Salt

An amount of compound 125 free base was heated at reflux and under stirring in absolute ethanol for 30 min allowing complete dissolution of the starting material (concentration of about 25 g/L).

After that time 1 equivalent of maleic acid was dissolved in ethanol (concentration of about 315 g/L) and added to the free base solution.

After 30 min at reflux to achieve complete salification, the stirring was slowed down and the heating was interrupted.

The mixture came back spontaneously at RT overnight allowing precipitation.

The day after the suspension was cooled at 0° C., stirred for 30 min at that temperature and then filtered on a glass fiber filter.

The reactor was then washed with the mother liquors and the suspension obtained was filtered on the existing panel.

The obtained material was then dried at 50° C. for 48 hours.

Example 4

Solubility of Compound 125 Salts and Free Base

The determination of solubility of compound 125 salts has been performed by means of the following procedure if no other conditions specified: known amounts of compound 125 salts or free base obtained by evaporation of a DMSO stock solution in a 96-well plate have been added of the below reported media in order to achieve a target concentration of 10 mg/mL or 20 mg/mL The obtained preparations have been shaken at RT for 30 minutes, filtered and analysed by means of HPLC.

The results are here below reported; the achievement of the target value (10 mg/ml or 20 mg/ml) is specified by the indication "or higher".

The solubility values of the compound 125 glycolate salt in different aqueous media were determined and found to be as follows:

6.2 mg/mL in 5% glucose solution; 10.0 mg/mL or higher in buffer solution pH 1.2 (chloride buffer) and buffer solution pH 4.5 (acetate buffer); 0.2 mg/mL in buffer solution pH 6.8 (phosphate buffer).

The solubility values of the compound 125 malonate salt in 5% glucose solution is 18.4 mg/mL.

The solubility values of the compound 125 tri-hydrochloride salt form I in 5% glucose solution is 10 mg/mL or higher.

The solubility values of the compound 125 di-hydrochloride salt in 5% glucose solution is 20 mg/mL or higher.

The solubility values of the compound 125 maleate salt form III in different aqueous media were determined and found to be as follows:

10.0 mg/mL or higher in 5% glucose solution; about 40.0 mg/mL in buffer solution pH 4.5 (acetate buffer); <0.1 mg/mL in buffer solution pH 6.8 (phosphate buffer).

The determination of solubility of compound 125 maleate salt form III in buffer solutions has been performed by addition of 10 mL of the medium to 40 mg of compound 125. The vials were mechanically shaken at 37° C. and protected from light. After 16 hours the samples were withdrawn and solubility assayed by means of a specific HPLC assay.

The solubility values of the compound 125 free base in different aqueous media were determined and found to be as follows:

solution <0.1 mg/mL in 5% glucose solution; 7.2 mg/mL in 50% polyethylene glycol 400 in 5% glucose solution; 0.8 mg/mL in 10% polysorbate 80 in 5% glucose solution; 10 mg/mL when formulated as hydrochloride in situ salt.

Example 5

Analytical Results by Means of Powder X-ray Diffraction (PXRD)

The compound 125 salts were characterized by powder X-Ray Diffraction (PXRD) performed using a Thermo/ARL XTRA apparatus, irradiating powder samples with a CuKα source (45 kV, 40 mA, 1.8 kW-Kα1 radiation, wavelength λ=1.54060 Angstrom) between 5° and 34° 2-theta at room temperature.

The scan rate was of 1.20°/min (0.020° step with count time of 1 seconds per step).

In the X-Ray diffractograms, the angles of diffraction 2-theta are plotted on the horizontal axis (x-axis) and the line intensity on the vertical (y-axis).

In the paragraphs defining the X-ray powder diffraction peaks for the crystalline forms of the salts and free base of compound 125, the term 'at about' is used in the expression ' . . . at about 2-theta angles reported in table . . . ' to indicate that the precise position of peaks (i.e. the recited 2-theta angle values) should not be construed as being absolute values because, as will be appreciated by those skilled in the art, the precise position of the peaks may vary slightly between one machine and another, from one sample to another, or as a result of slight variations in measurement conditions utilised.

It is also stated in the preceding paragraphs that the crystalline forms of the salts and free base of compound 125 provide X-ray powder diffraction patterns 'substantially' the same as the X-ray powder diffraction patterns shown in FIGS. 1, 2, 3, 4, 5, 6, 7, 8, 9, 10, 11, 12, 13, 14 and 15 have substantially the most prominent peaks at the 2-theta angle values shown in tables 1, 2, 3, 4, 5, 6, 7, 8, 9, 10 and 11. It shall be appreciated that the use of the term 'substantially' in this context is also intended to indicate that the 2-theta angle values of the X-ray powder diffraction patterns may vary slightly from one machine to another, from one sample to another, or as a result of slight variations in measurement conditions utilised, so the peak positions shown in the figures or quoted in the tables are again not to be construed as absolute values.

In this regard, it is known in the art that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation.

For example, persons skilled in the art of X-ray powder diffraction will realise that the relative intensity of peaks can be affected by, for example, grains above 30 microns in size and non-unitary aspect ratios, which may affect analysis of samples.

The skilled person will also realise that the position of reflections can be affected by the precise height at which the sample sits in the diffractometer and the zero calibration of the diffractometer.

The surface planarity of the sample may also have a small effect.

Hence a person skilled in the art will appreciate that the diffraction pattern data presented herein is not to be construed as absolute (for further information see "Fundamentals of Powder Diffraction and Structural Characterization, Pecharsky and Zavalij, Kluwer Academic Publishers, 2003). Therefore, it shall be understood that the crystalline form of the salts and free base of compound 125 described in the present invention is not limited to the crystals that provide X-ray powder diffraction patterns identical to the X-ray powder diffraction patterns shown in FIG. 1 and any crystals providing X-ray powder diffraction patterns substantially the same as that shown in FIG. 1 fall within the scope of the present invention.

A person skilled in the art of X-ray powder diffraction is able to judge the substantial identity of X-ray powder diffraction patterns.

Generally, a measurement error of a diffraction angle in an X-ray powder diffractogram is about 2-theta=0.5 deg or less (or, more suitably, about 2-theta=0.2 deg or less) and such degree of a measurement error should be taken into account when considering the X-ray powder diffraction pattern in FIGS. 1, 2, 3, 4, 5, 6, 7, 8, 9, 10, 11, 12, 13, 14 and 15, and when interpreting the peak positions referred to both in the text and in tables 1, 2, 3, 4, 5, 6, 7, 8, 9, 10 and 11.

Therefore, where it is stated, for example, that the salts and free base of compound 125 have an X-ray powder diffraction pattern with at least one specific peak at about 2-theta=22.8 deg (or any one of the other mentioned angles) then this can be interpreted as being 2-theta=15.2 deg plus or minus 0.5 deg, or 2-theta=15.2 deg plus or minus 0.2 deg.

FIGS. 1 to 5 reports powder X-Ray diffractograms of the salts of compound 125 isolated at low scale as described in example 1, and of the free base.

The main X-ray diffraction peaks of compound 125 glycolate salt (form I), malonate salt (form I), maleate salt (form I, form II and form III) are reported in FIGS. 7, 8, 9, 10, 11, 12 and 13 that reports examples of powder X-ray diffractograms of the salts of compound 125 obtained at a larger scale according to examples 2, 3 and 4 (glycolate, malonate and maleate salts).

The main X-ray diffraction peaks 2-theta angles of compound 125 glycolate salt (form I), malonate salt (form I), tri-hydrochloride salt (form I), di-hydrochloride salt (form I), hydrochloride salt (form I), maleate salt (form I, form II and form III), compound 125 free base (form I and form II) are here below summarized in the following tables 2, 3, 4, 5, 6, 7, 8, 9, 10 and 11.

TABLE 2

Compound 125 glycolate salt

| Position (deg) | Intensity (CPS) | Relative Intensity (%) |
|---|---|---|
| 6.6 | 525.9 | 16.5 |
| 9.7 | 504.5 | 15.8 |
| 10.6 | 277.1 | 8.7 |
| 10.9 | 190.9 | 6.0 |
| 11.8 | 2122.7 | 66.6 |
| 12.2 | 1133.9 | 35.6 |
| 12.7 | 852.3 | 26.7 |
| 13.1 | 130.6 | 4.1 |
| 13.8 | 74.4 | 2.3 |
| 15.6 | 122.5 | 3.8 |
| 16.1 | 525.5 | 16.5 |
| 16.5 | 516.8 | 16.2 |
| 17.3 | 198.8 | 6.2 |
| 17.5 | 720.2 | 22.6 |
| 18.1 | 86.9 | 2.7 |
| 19.4 | 3187.8 | 100.0 |
| 20.1 | 312.9 | 9.8 |
| 20.4 | 355.5 | 11.2 |
| 20.7 | 99.6 | 3.1 |
| 21.0 | 189.7 | 6.0 |
| 21.2 | 280.3 | 8.8 |
| 21.9 | 1167.1 | 36.6 |
| 22.5 | 386.5 | 12.1 |
| 22.8 | 240.3 | 7.5 |
| 23.6 | 1620.6 | 50.8 |
| 23.9 | 1419.2 | 44.5 |
| 25.9 | 1221.0 | 38.3 |
| 27.8 | 859.2 | 27.0 |
| 28.3 | 164.6 | 5.2 |
| 29.2 | 152.9 | 4.8 |
| 30.3 | 196.2 | 6.2 |
| 30.7 | 203.4 | 6.4 |
| 31.1 | 107.6 | 3.4 |
| 32.5 | 156.7 | 4.9 |
| 33.1 | 167.6 | 5.3 |

TABLE 3

Compound 125 malonate salt

| Position (deg) | Intensity (CPS) | Relative Intensity (%) |
|---|---|---|
| 5.9 | 82.1 | 14.1 |
| 7.8 | 55.7 | 9.6 |
| 10.9 | 79.1 | 13.6 |
| 11.5 | 280.2 | 48.1 |
| 12.4 | 155.1 | 26.6 |
| 13.9 | 73.8 | 12.7 |
| 14.3 | 378.3 | 64.9 |
| 14.6 | 83.1 | 14.3 |
| 15.3 | 53.7 | 9.2 |
| 15.8 | 125.1 | 21.5 |
| 16.1 | 38.8 | 6.7 |
| 16.4 | 48.7 | 8.4 |
| 17.3 | 29.9 | 5.1 |
| 18.2 | 32.8 | 5.6 |
| 18.8 | 101.7 | 17.5 |
| 20.9 | 582.6 | 100.0 |
| 21.8 | 221.0 | 37.9 |
| 22.7 | 155.2 | 26.6 |
| 23.0 | 250.6 | 43.0 |
| 23.7 | 37.5 | 6.4 |
| 24.8 | 108.7 | 18.7 |
| 25.2 | 18.6 | 3.2 |
| 25.5 | 22.7 | 3.9 |
| 27.4 | 45.8 | 7.9 |
| 29.2 | 82.5 | 14.2 |

TABLE 3-continued

Compound 125 malonate salt

| Position (deg) | Intensity (CPS) | Relative Intensity (%) |
|---|---|---|
| 30.4 | 24.8 | 4.3 |
| 33.1 | 34.9 | 6.0 |

TABLE 4

Compound 125 tri-hydrochloride salt, Form I

| Position (deg) | Intensity (CPS) | Relative Intensity (%) |
|---|---|---|
| 5.4 | 183.0 | 11.1 |
| 7.7 | 1483.0 | 90.0 |
| 8.2 | 1642.0 | 99.6 |
| 10.6 | 245.7 | 14.9 |
| 11.1 | 1648.3 | 100.0 |
| 12.2 | 95.6 | 5.8 |
| 13.1 | 234.0 | 14.2 |
| 14.6 | 138.4 | 8.4 |
| 15.3 | 76.9 | 4.7 |
| 15.6 | 72.7 | 4.4 |
| 16.2 | 25.6 | 1.6 |
| 17.3 | 182.0 | 11.0 |
| 17.6 | 316.5 | 19.2 |
| 18.4 | 37.0 | 2.3 |
| 20.3 | 141.4 | 8.6 |
| 21.2 | 196.6 | 11.9 |
| 21.6 | 48.8 | 3.0 |
| 22.1 | 561.9 | 34.1 |
| 22.6 | 182.1 | 11.1 |
| 23.1 | 195.4 | 11.9 |
| 23.2 | 244.8 | 14.9 |
| 24.4 | 268.1 | 16.3 |
| 24.9 | 167.1 | 10.1 |
| 25.1 | 318.6 | 19.3 |
| 25.4 | 160.4 | 9.7 |
| 26.4 | 641.3 | 38.9 |
| 28.1 | 343.9 | 20.9 |
| 28.6 | 104.3 | 6.3 |
| 30.9 | 229.2 | 13.9 |
| 31.9 | 387.6 | 23.5 |
| 33.5 | 98.6 | 6.0 |

TABLE 5

Compound 125 di-hydrochloride salt

| Position (deg) | Intensity (CPS) | Relative Intensity (%) |
|---|---|---|
| 5.3 | 236.3 | 12.0 |
| 7.7 | 1965.7 | 100.0 |
| 8.1 | 1922.5 | 97.8 |
| 10.6 | 288.0 | 14.7 |
| 11.0 | 1694.4 | 86.2 |
| 13.1 | 263.9 | 13.4 |
| 14.6 | 210.1 | 10.7 |
| 15.3 | 77.1 | 3.9 |
| 15.5 | 107.8 | 5.5 |
| 17.3 | 139.2 | 7.1 |
| 17.6 | 279.9 | 14.2 |
| 18.5 | 56.2 | 2.9 |
| 20.1 | 47.1 | 2.4 |
| 20.3 | 175.7 | 8.9 |
| 21.2 | 185.8 | 9.5 |
| 21.5 | 115.8 | 5.9 |
| 22.1 | 545.4 | 27.8 |
| 22.6 | 233.9 | 11.9 |

TABLE 5-continued

Compound 125 di-hydrochloride salt

| Position (deg) | Intensity (CPS) | Relative Intensity (%) |
|---|---|---|
| 23.0 | 270.8 | 13.8 |
| 23.2 | 240.9 | 12.3 |
| 23.4 | 91.7 | 4.7 |
| 24.3 | 312.2 | 15.9 |
| 24.9 | 200.5 | 10.2 |
| 25.1 | 523.9 | 26.7 |
| 25.4 | 209.4 | 10.7 |
| 26.4 | 526.5 | 26.8 |
| 27.2 | 83.2 | 4.2 |
| 28.1 | 296.7 | 15.1 |
| 28.5 | 169.9 | 8.6 |
| 30.8 | 258.4 | 13.1 |
| 31.8 | 445.9 | 22.7 |
| 33.5 | 155.1 | 7.9 |

TABLE 6

Compound 125 hydrochloride salt

| Position (deg) | Intensity (CPS) | Relative Intensity (%) |
|---|---|---|
| 4.6 | 191.7 | 53.9 |
| 5.2 | 201.1 | 56.6 |
| 5.4 | 172.8 | 48.6 |
| 7.6 | 49.7 | 14.0 |
| 8.1 | 355.4 | 100.0 |
| 8.4 | 111.5 | 31.4 |
| 9.4 | 112.8 | 31.7 |
| 10.2 | 115.5 | 32.5 |
| 10.6 | 176.1 | 49.5 |
| 11.1 | 73.5 | 20.7 |
| 12.0 | 23.8 | 6.7 |
| 12.4 | 70.4 | 19.8 |
| 13.5 | 76.4 | 21.5 |
| 13.8 | 59.7 | 16.8 |
| 14.0 | 74.2 | 20.9 |
| 14.6 | 110.4 | 31.1 |
| 14.8 | 45.2 | 12.7 |
| 16.7 | 20.2 | 5.7 |
| 17.0 | 40.7 | 11.5 |
| 17.5 | 51.5 | 14.5 |
| 18.7 | 43.6 | 12.3 |
| 19.2 | 41.4 | 11.7 |
| 20.1 | 44.4 | 12.5 |
| 21.0 | 151.9 | 42.7 |
| 23.5 | 159.6 | 44.9 |
| 24.0 | 36.4 | 10.3 |
| 24.9 | 221.1 | 62.2 |
| 26.2 | 69.6 | 19.6 |
| 26.9 | 32.9 | 9.3 |
| 27.9 | 37.3 | 10.5 |
| 28.4 | 26.1 | 7.3 |

TABLE 7

Compound 125 maleate salt Form I

| Position (deg) | Intensity (CPS) | Relative Intensity (%) |
|---|---|---|
| 5.3 | 242.3 | 20.3 |
| 6.0 | 435.1 | 36.4 |
| 11.3 | 167.8 | 14.0 |
| 11.9 | 271.5 | 22.7 |
| 12.7 | 257.1 | 21.5 |
| 13.5 | 534.7 | 44.7 |

TABLE 7-continued

Compound 125 maleate salt Form I

| Position (deg) | Intensity (CPS) | Relative Intensity (%) |
|---|---|---|
| 14.5 | 421.6 | 35.3 |
| 14.7 | 114.9 | 9.6 |
| 15.9 | 116.2 | 9.7 |
| 16.6 | 175.8 | 14.7 |
| 16.9 | 219.6 | 18.4 |
| 17.9 | 835.6 | 69.9 |
| 19.4 | 265.1 | 22.2 |
| 20.9 | 1195.1 | 100.0 |
| 22.9 | 295.7 | 24.7 |
| 23.2 | 1106.5 | 92.6 |
| 23.9 | 138.4 | 11.6 |
| 24.7 | 415.8 | 34.8 |
| 25.0 | 176.2 | 14.8 |
| 27.0 | 126.0 | 10.6 |
| 28.1 | 178.7 | 15.0 |
| 30.9 | 90.7 | 7.6 |
| 32.2 | 70.5 | 5.9 |

TABLE 8

Compound 125 maleate salt Form II

| Position (deg) | Intensity (CPS) | Relative Intensity (%) |
|---|---|---|
| 4.8 | 2637.5 | 100.0 |
| 5.8 | 104.3 | 4.0 |
| 8.3 | 41.9 | 1.6 |
| 8.6 | 32.8 | 1.3 |
| 9.6 | 439.1 | 16.7 |
| 10.8 | 103.0 | 3.9 |
| 11.6 | 525.6 | 19.9 |
| 12.1 | 75.4 | 2.9 |
| 13.0 | 319.6 | 12.1 |
| 14.4 | 261.7 | 9.9 |
| 15.7 | 598.3 | 22.7 |
| 16.0 | 766.1 | 29.1 |
| 16.7 | 516.7 | 19.6 |
| 17.6 | 181.5 | 6.9 |
| 18.4 | 49.9 | 1.9 |
| 18.7 | 98.2 | 3.7 |
| 19.3 | 606.7 | 23.0 |
| 20.9 | 735.6 | 27.9 |
| 21.3 | 661.9 | 25.1 |
| 22.1 | 1236.0 | 46.9 |
| 22.7 | 307.4 | 11.7 |
| 23.3 | 456.5 | 17.3 |
| 24.0 | 192.4 | 7.3 |
| 24.3 | 71.6 | 2.7 |
| 25.7 | 424.1 | 16.1 |
| 27.7 | 514.0 | 19.5 |
| 30.1 | 286.5 | 10.9 |
| 32.2 | 158.2 | 6.0 |

TABLE 9

Compound 125 maleate salt Form III

| Position (deg) | Intensity (CPS) | Relative Intensity (%) |
|---|---|---|
| 5.1 | 222.0 | 9.1 |
| 6.0 | 441.1 | 18.1 |
| 8.3 | 68.2 | 2.8 |
| 9.3 | 43.0 | 1.8 |
| 10.0 | 79.3 | 3.3 |
| 11.2 | 246.4 | 10.1 |

TABLE 9-continued

Compound 125 maleate salt Form III

| Position (deg) | Intensity (CPS) | Relative Intensity (%) |
|---|---|---|
| 11.8 | 280.8 | 11.5 |
| 12.3 | 373.9 | 15.3 |
| 13.3 | 543.8 | 22.3 |
| 14.3 | 414.3 | 17.0 |
| 14.7 | 60.2 | 2.5 |
| 15.9 | 204.0 | 8.4 |
| 16.3 | 520.7 | 21.3 |
| 16.9 | 126.6 | 5.2 |
| 17.8 | 668.4 | 27.4 |
| 18.2 | 173.2 | 7.1 |
| 19.4 | 255.3 | 10.5 |
| 19.8 | 250.7 | 10.3 |
| 20.2 | 223.7 | 9.2 |
| 20.8 | 773.5 | 31.7 |
| 21.8 | 144.8 | 5.9 |
| 22.8 | 2442.6 | 100.0 |
| 23.7 | 271.2 | 11.1 |
| 24.3 | 275.9 | 11.3 |
| 24.7 | 81.4 | 3.3 |
| 24.9 | 204.9 | 8.4 |
| 25.9 | 115.9 | 4.7 |
| 26.4 | 390.9 | 16.0 |
| 27.6 | 333.8 | 13.7 |
| 28.1 | 140.8 | 5.8 |
| 31.1 | 85.5 | 3.5 |
| 32.0 | 73.8 | 3.0 |

TABLE 10

Compound 125 free base, Form I

| Position (deg) | Intensity (CPS) | Relative Intensity (%) |
|---|---|---|
| 5.6 | 677.9 | 38.4 |
| 6.3 | 22.0 | 1.3 |
| 7.2 | 75.5 | 4.3 |
| 9.3 | 1764.7 | 100.0 |
| 9.7 | 12.4 | 0.7 |
| 10.9 | 122.6 | 7.0 |
| 11.4 | 865.2 | 49.0 |
| 12.5 | 64.0 | 3.6 |
| 13.0 | 91.2 | 5.2 |
| 14.4 | 398.6 | 22.6 |
| 14.5 | 127.8 | 7.2 |
| 16.4 | 105.5 | 6.0 |
| 17.3 | 169.5 | 9.6 |
| 18.6 | 83.1 | 4.7 |
| 19.3 | 285.0 | 16.2 |
| 19.6 | 209.9 | 11.9 |
| 21.6 | 94.8 | 5.4 |
| 21.8 | 111.3 | 6.3 |
| 22.4 | 134.4 | 7.6 |
| 24.4 | 63.4 | 3.6 |
| 25.5 | 122.5 | 6.9 |
| 28.3 | 25.0 | 1.4 |
| 28.7 | 35.9 | 2.0 |

TABLE 11

Compound 125 free base, form II

| Position (deg) | Intensity (CPS) | Relative Intensity (%) |
|---|---|---|
| 6.1 | 324.5 | 35.1 |
| 8.8 | 69.3 | 7.5 |

TABLE 11-continued

Compound 125 free base, form II

| Position (deg) | Intensity (CPS) | Relative Intensity (%) |
|---|---|---|
| 10.3 | 116.7 | 12.6 |
| 11.4 | 181.8 | 19.7 |
| 11.9 | 925.3 | 100.0 |
| 12.6 | 174.1 | 18.8 |
| 14.3 | 70.2 | 7.6 |
| 14.5 | 100.6 | 10.9 |
| 16.0 | 26.2 | 2.8 |
| 16.4 | 39.7 | 4.3 |
| 17.7 | 41.4 | 4.5 |
| 18.0 | 38.4 | 4.2 |
| 18.5 | 208.0 | 22.5 |
| 18.9 | 108.4 | 11.7 |
| 20.3 | 363.7 | 39.3 |
| 21.1 | 54.1 | 5.9 |
| 22.2 | 76.9 | 8.3 |
| 22.7 | 99.6 | 10.8 |
| 23.0 | 118.6 | 12.8 |
| 23.9 | 64.3 | 7.0 |
| 24.2 | 86.8 | 9.4 |
| 24.8 | 113.0 | 12.2 |
| 25.7 | 106.5 | 11.5 |
| 27.0 | 82.7 | 8.9 |
| 28.0 | 34.0 | 3.7 |
| 29.3 | 12.0 | 1.3 |
| 30.0 | 11.0 | 1.2 |
| 31.0 | 11.4 | 1.2 |
| 31.5 | 16.3 | 1.8 |
| 32.2 | 27.6 | 3.0 |

Example 6

Analytical Results by Means of Differential Scanning Calorimetry (DSC)

DSC analyses were carried out with a Perkin-Elmer DSC-7 apparatus. Aluminum DSC pans were loaded with about 2 mg of sample. The temperature range of the analyses was between 30° C. and a maximum value of 300° C. The samples were analyzed under nitrogen flow at a heating rate of 10° C./min.

Figure 16:
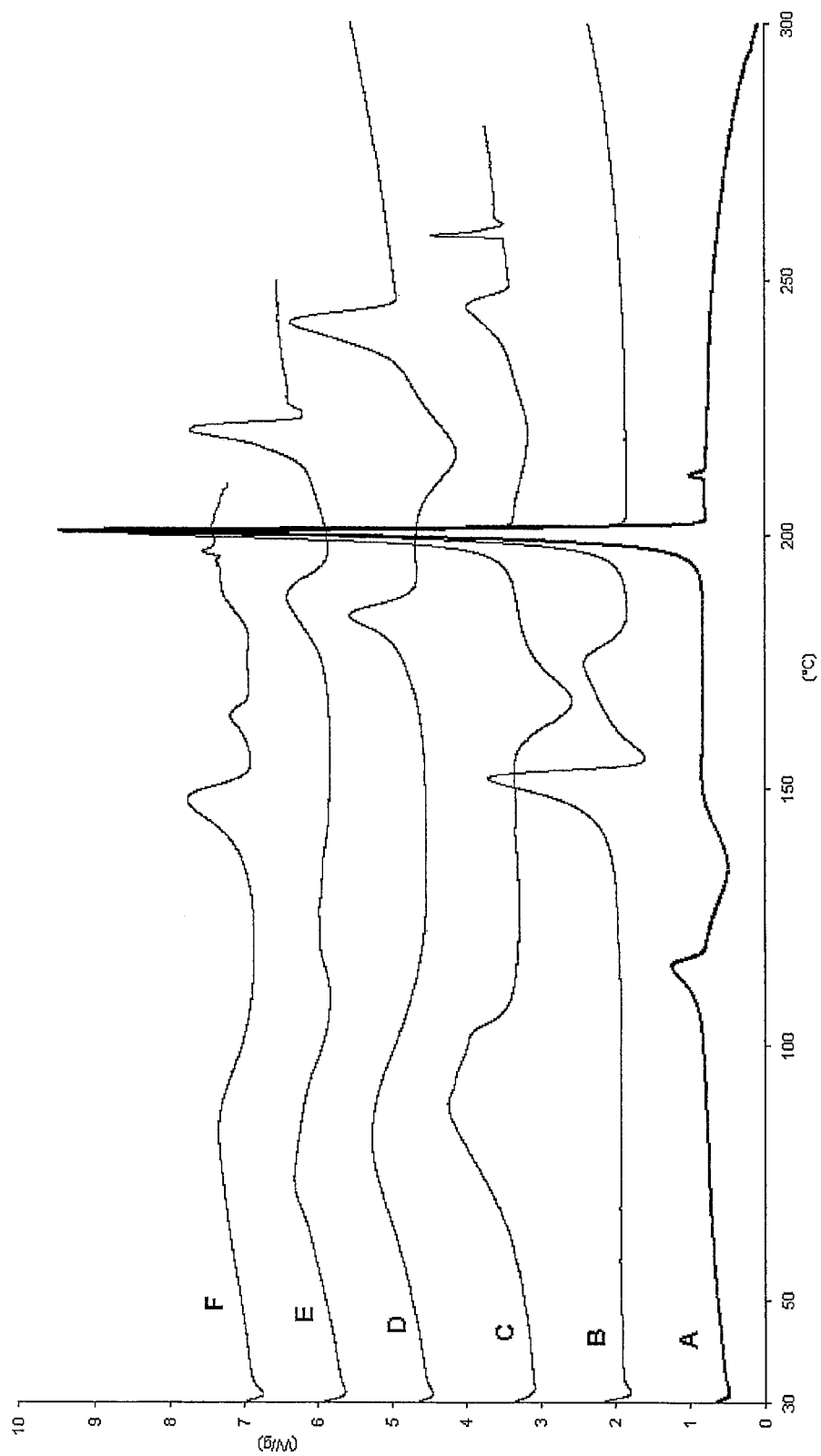
FIG. 16 shows the DSC thermograms of compound 125 free base form I (A) and the following salts: malonate form I (B), phosphate form I (C), mesylate form I (D), fumarate semi-crystalline form I (E), L-malate form I (F). The thermogram reports temperature (° C.) on the x axis while heat flow (mW) is reported on the y axis.
Figure 17:
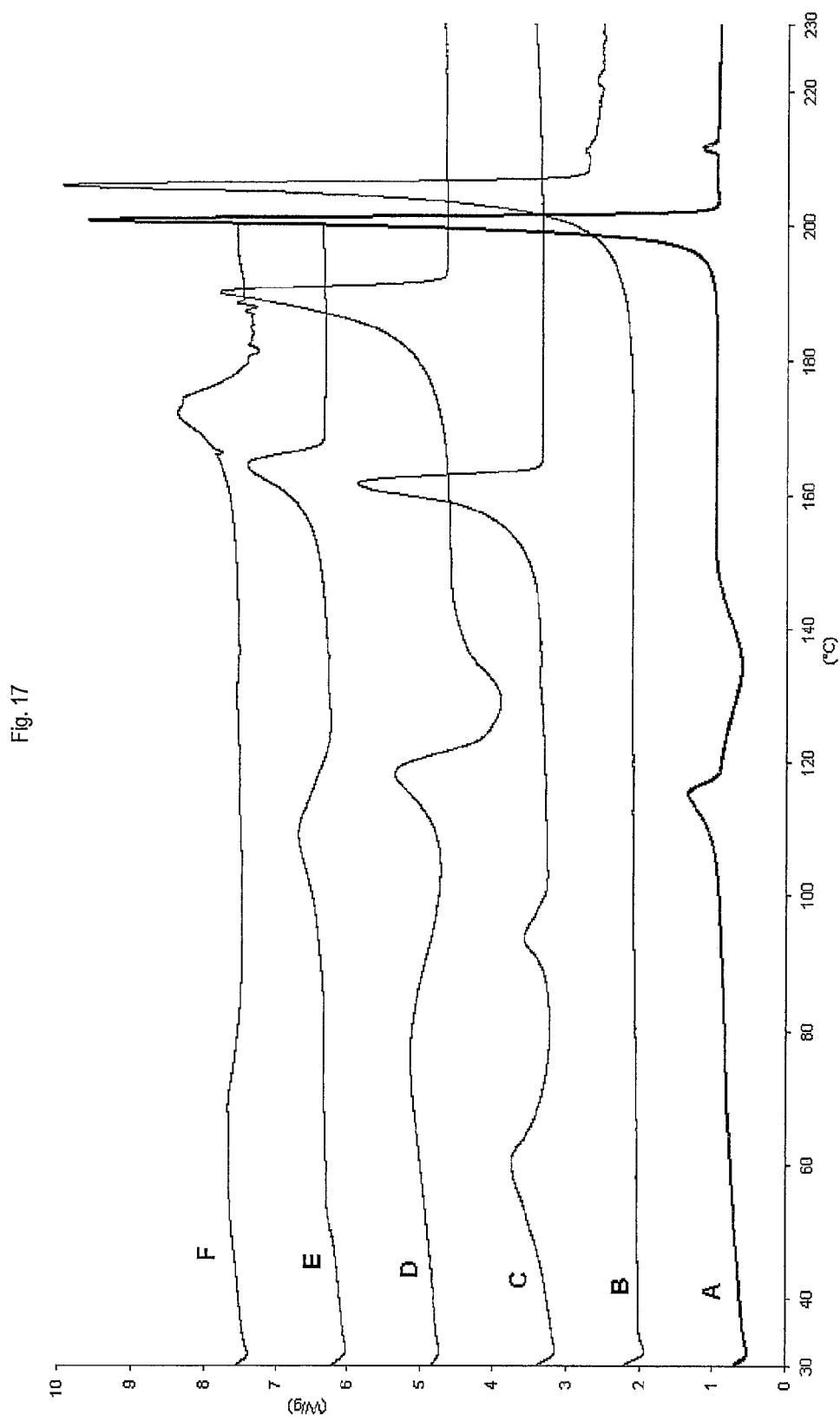
FIG. 17 shows the DSC thermograms of compound 125 free base form I (A) and the following salts: glycolate form I (B), adipate form I (C), L-lactate form I (D), succinate form I (E) and maleate form II (F) salts.
Figure 18:
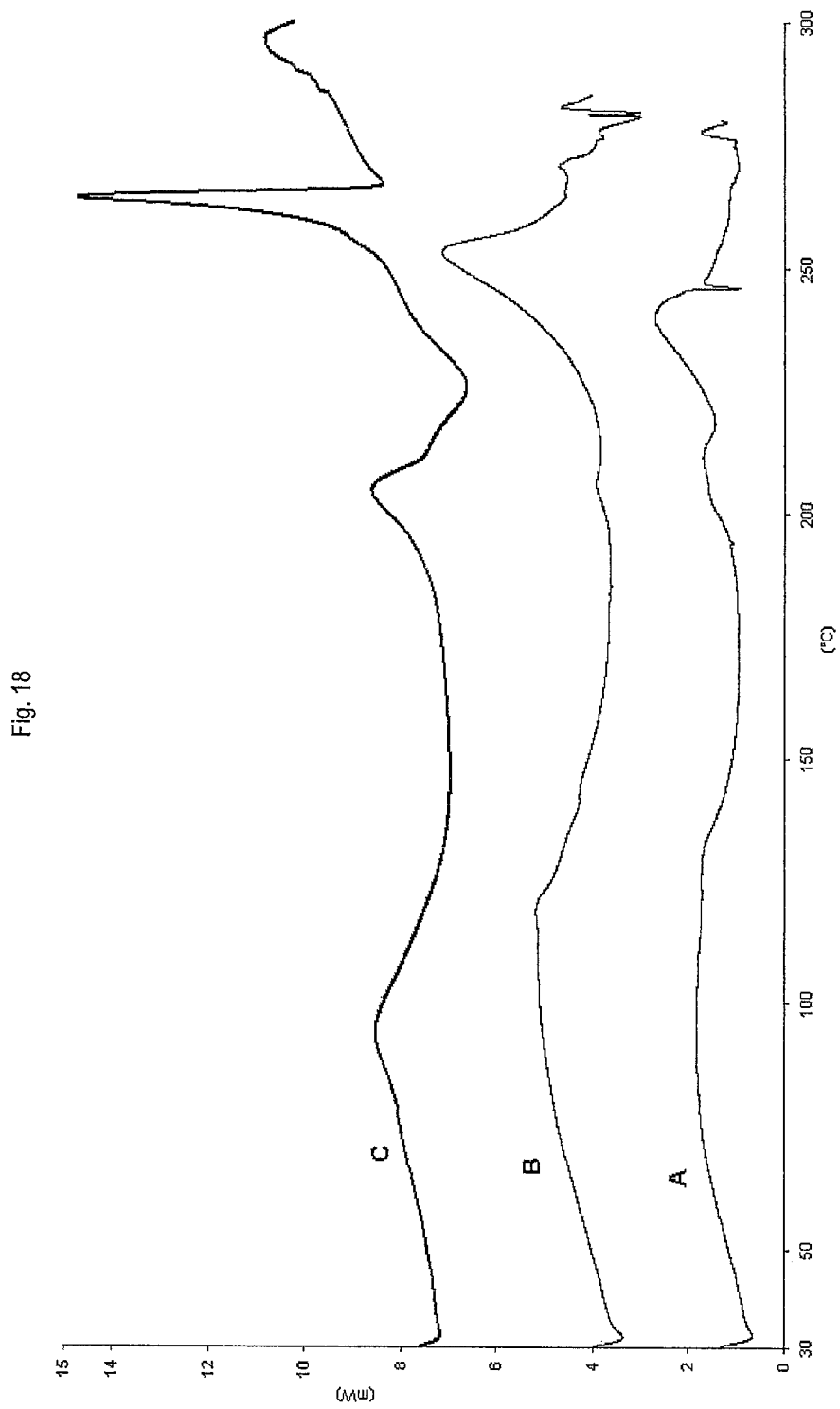
FIG. 18 shows the DSC thermograms of compound 125 tri-hydrochloride form I (A), di-hydrochloride form I (B) and hydrochloride form I (C).

FIGS. 16, 17, 18 report DSC thermograms of the salts and free base of compound 125 isolated at low scale as described in example 1 and hydrochloride salts obtained in different ratios.

Figure 19:
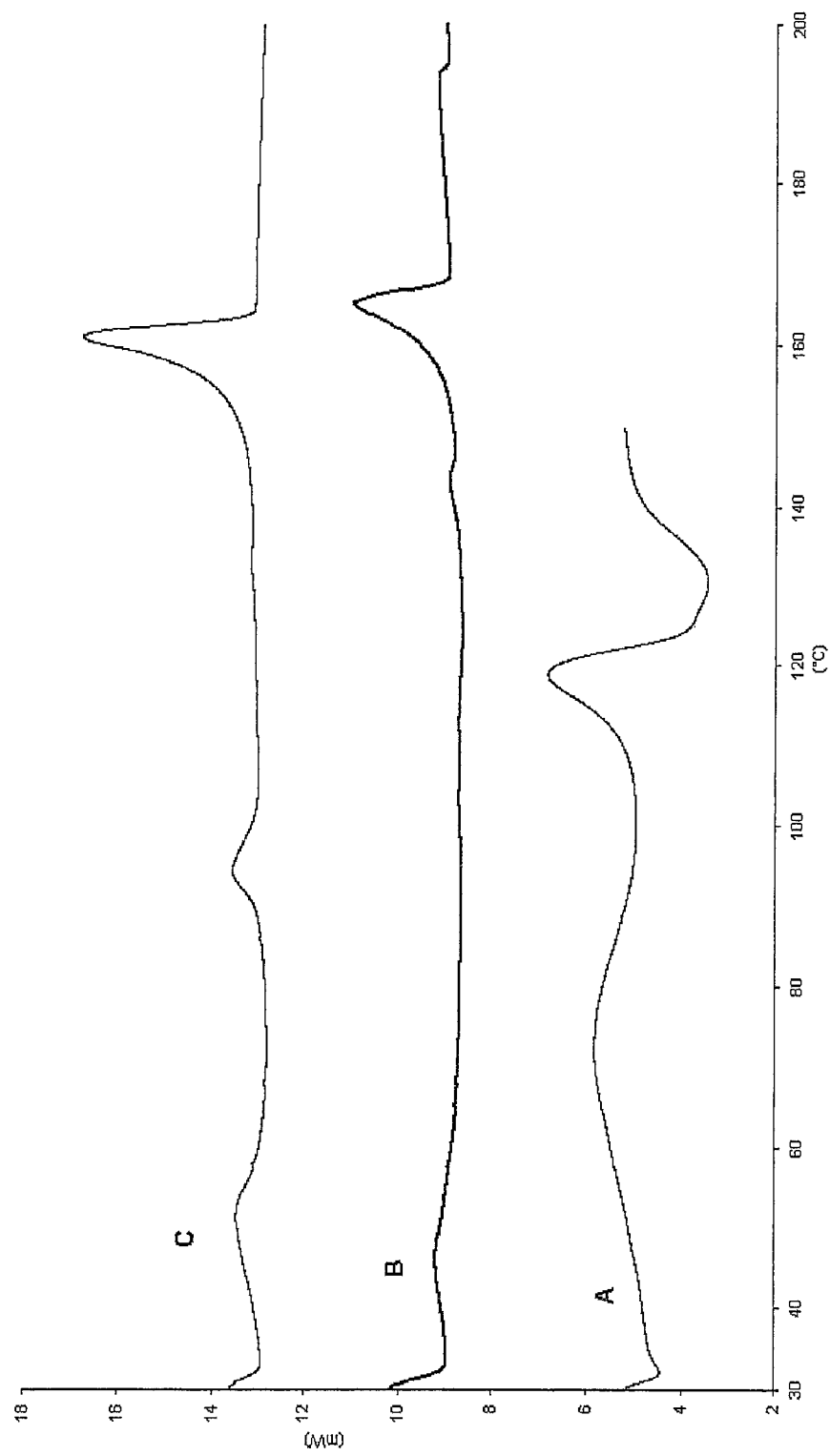
FIG. 19 reports DSC thermograms of compound 125 L-lactate form I (A), succinate form I (B) and adipate form I (C) salts submitted to additional drying as described in example 6.

FIG. 19 reports DSC thermograms of L-lactate form I (A), succinate form I (B) and adipate form I (C) salts of compound 125 isolated at low scale as described in example 1 and after a further drying process at 65° C. under vacuum. The comparison with the original DSC thermograms (reported in FIG. 17) shows their nature of hydrated forms. In fact it can be observed that L-Lactate and adipate salts DSC profile maintain the initial thermal behavior including thermal features related to desolvation and/or solid state transition. On the other hand succinate salt DSC profile is significantly modified by drying with appearance of a new thermal transition.

It is observed that the thermal treatment operated in the DSC experiment of L-lactate and adipate salts operates a conversion into an anhydrous form of these salts showing a single melting peak.

Figure 20:
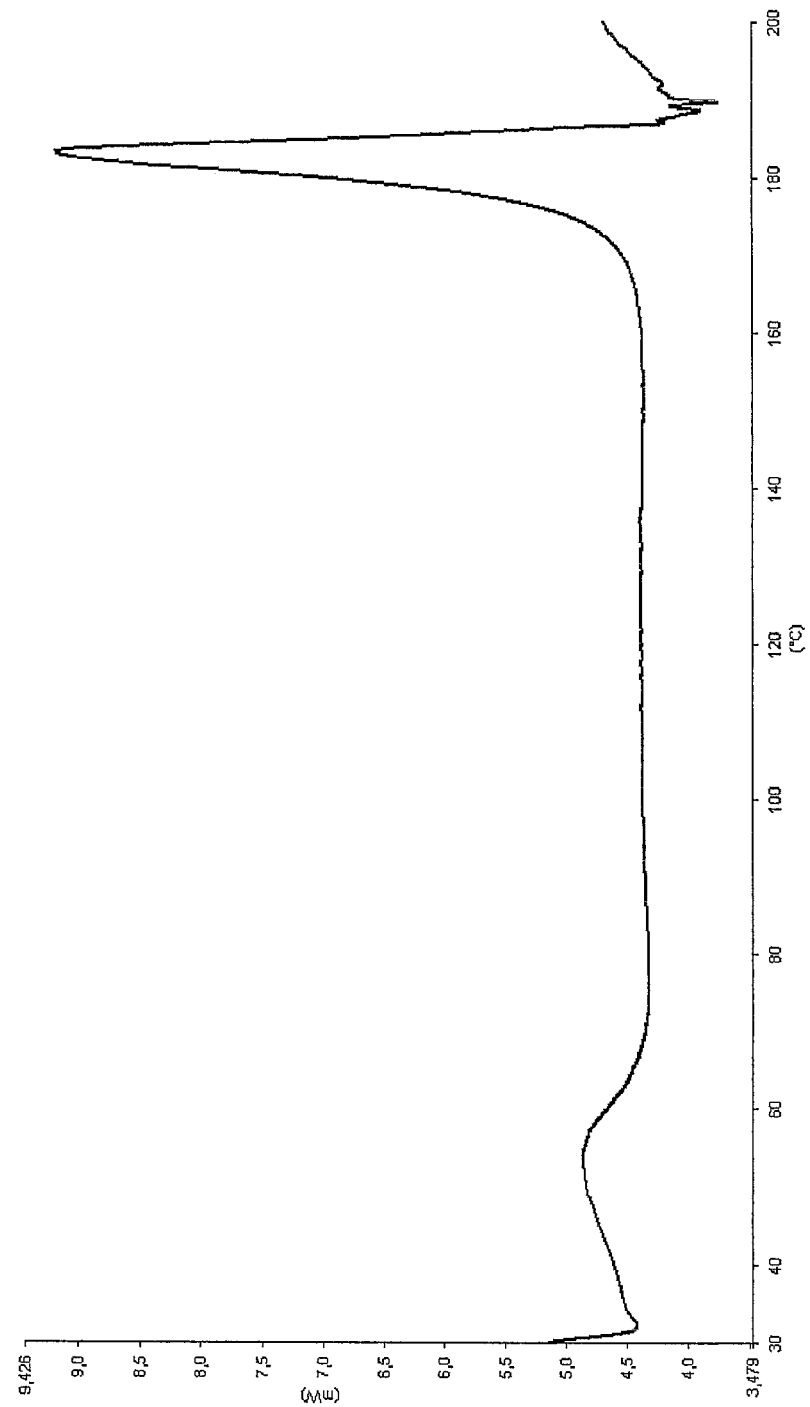
FIG. 20 reports a typical DSC thermogram of compound 125 maleate salt.

FIG. 20 reports a typical DSC thermograms of compound 125 maleate salt obtained according example 1 and characterizing both form I and III. For compound 125 maleate salt the observed melting endotherm was at approximately 183° C. (peak temperature) showing ΔHf of approximately 65 J/g. A dehydration endotherm is commonly detected in the initial part of the DSC thermogram depending on the equilibration of the water uptake of the material.

It will be understood that the onset and/or peak temperature values of the DSC may vary slightly from one machine to another, one method to another or from one sample to another, and so the values quoted are not to be construed as absolute. In fact, observed temperatures will depend on the rate of temperature change as well as sample preparation technique and the particular instrument employed. It will be estimated and taken into account that the temperature values obtained applying such different conditions may vary by plus or minus about 4° C.

Example 7

Analytical Results by Means of Thermogravimetric Analysis (TGA)

TGA analyses were carried out with a Perkin-Elmer TGA-7 apparatus. Aluminum DSC pans were loaded with 5÷10 mg of sample. The temperature range of the analyses was between 30° C. and a maximum value of about 200° C. The samples were analyzed under nitrogen flow (to eliminate oxidative and pyrolitic effects) at a heating rate of 2° C./min.

Figure 21:
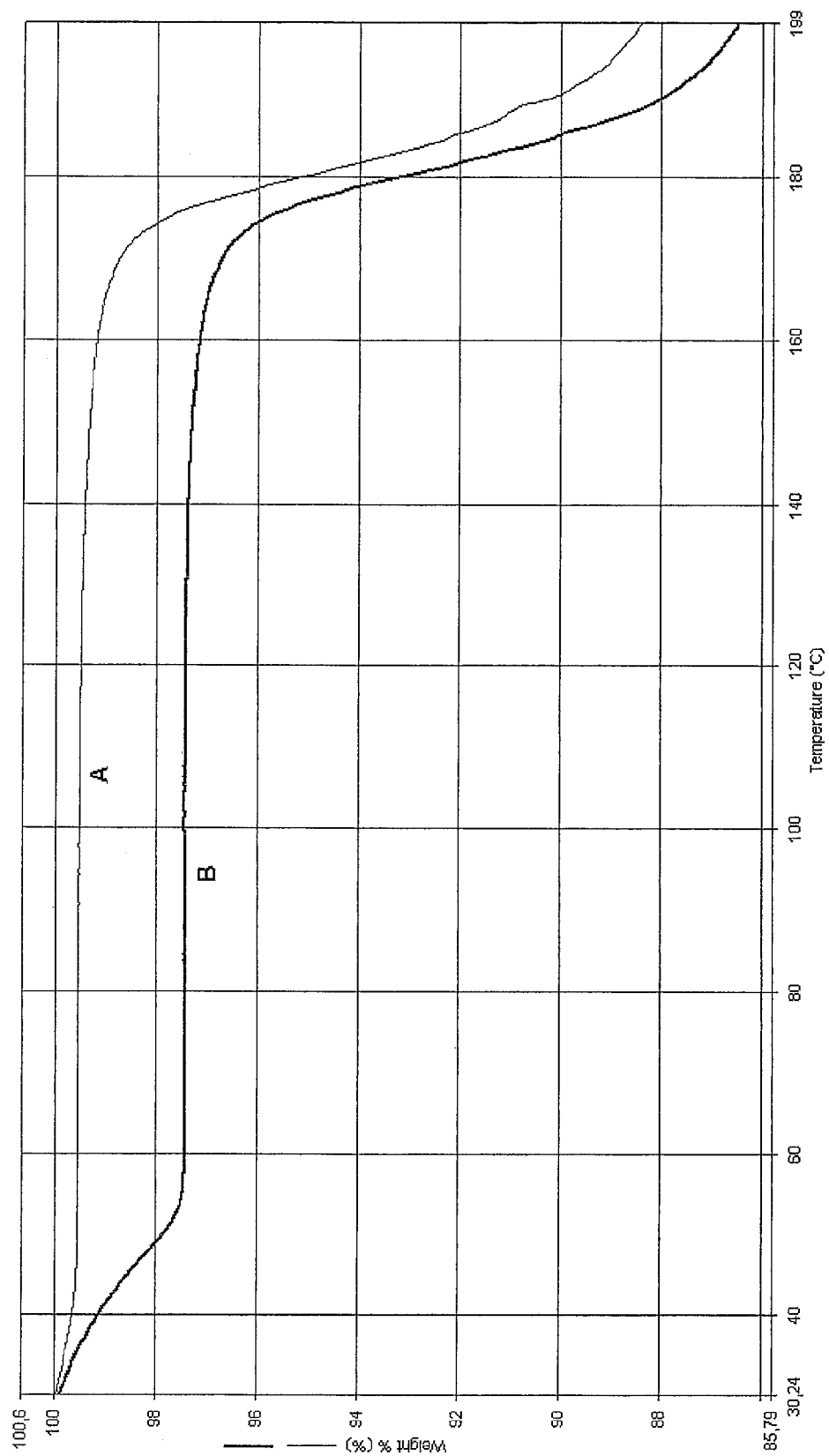
FIG. 21 reports a TGA thermogram of compound 125 maleate salt (A) and a TGA thermogram of compound 125 maleate salt submitted for example to equilibration by means of e.g. a hygroscopicity test (DVS) similar to the process described in example 8. The TGA thermogram reports temperature (° C.) on the x axis while percent weight (%) is reported on the y axis.

FIG. 21 reports typical TGA thermograms of compound 125 maleate salt obtained according to example 1 and characterizing the behavior of both form I and III when dehydrated (A) and equilibrated e.g. after a DVS sorption ramp (B). The weight loss step detected within 60° C. can be related to the dehydration endotherm commonly detected in the initial part of the DSC thermogram depending on the equilibration of the water uptake of the material.

Example 8

Analytical Results by Means of Dynamic Vapour Sorption (DVS)

The water uptake of compound 125 salts and free base was investigated by submitting a sample of such substances to a hygroscopicity test by means of a DVS 1000 (SMS). The apparatus is a "controlled atmosphere microbalance" where the weighed sample is exposed to programmed variations of the relative humidity (RH) at a constant and controlled temperature. The measured parameters (weight, time and RH), reported in Excel worksheets, allow obtaining hygroscopicity curves over the tested RH range.

Sorption/desorption cycles between 0% and 90% RH can be performed at controlled temperature of 25° C. Progressive variations of RH can be of 10% and 3%; they are operated by the software at the equilibration of the sample weight. This condition can be defined at a constant rate of percent weight variation e.g. 0.005%/min. The experimental results are reported both as in the DVS Isotherm Reports and Isotherm Plots. An example of the water uptake of compound 125 maleate salt during a DVS sorption ramp is here below summarized in the following table 12.

TABLE 12

Compound 125 Maleate salt DVS sorption data

| Relative Humidity (%) | Water uptake (%) |
|---|---|
| 0.0 | 0.0 |
| 10.0 | 0.1 |
| 20.0 | 0.2 |
| 30.0 | 1.9 |
| 40.0 | 2.5 |

TABLE 12-continued

Compound 125 Maleate salt DVS sorption data

| Relative Humidity (%) | Water uptake (%) |
|---|---|
| 50.0 | 2.7 |
| 60.0 | 2.8 |
| 70.0 | 2.8 |
| 80.0 | 2.9 |
| 90.0 | 3.1 |

Example 9

NMR Identification Analyses

The $^1$H NMR experiments were performed at a constant temperature of 28° C., on a Varian Inova 500 spectrometer operating at 499.8 MHz. A small amount of each sample was dissolved in 0.75 mL of DMSO-d6 and transferred into a 5-mm NMR tube for subsequent analysis. The analysis allows confirming the expected chemical structure of both molecule and counterions.

Example 10

Percent Compositions of a Formulation for Oral Use

| Ingredient | Range % |
|---|---|
| Compound 125 | 5-70 |
| Monohydrate Lactose | 25-95 |
| Magnesium Stearate | 0.05-2.5 |
| Colloidal Silicon Dioxide | 0.05-1 |

The person skilled in the art will appreciate from the above described data and examples that the new salts of compound 125 described in the invention are a new, improved and valuable tool in therapy.

The invention claimed is:

1. A salt of compound 125, or a crystal form of the salt of compound 125, having the following formula:

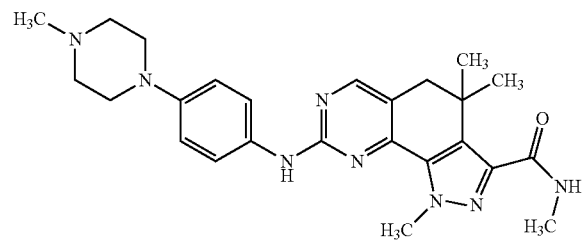 [SMILES: CNC(=O)c1nn(C)c2c1C(C)(C)Cc1cnc(Nc3ccc(N4CCN(C)CC4)cc3)nc1-2]

selected from maleate, malonate and glycolate salt.

2. A hydrate of a salt of compound 125 having the following formula:

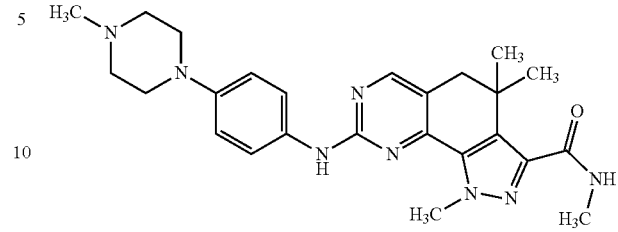

selected from maleate, malonate and glycolate salt.

3. A crystalline form or a hydrate of the maleate salt of compound 125 having the following formula:

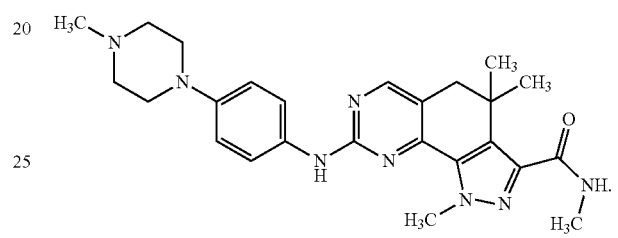

4. A crystal form of the compound 125 having the following formula:

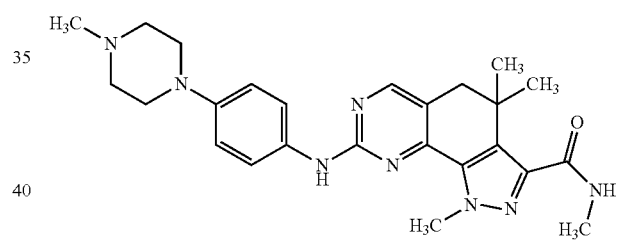

selected from maleate, malonate and glycolate salt as a free base.

5. A medicament comprising any salt of the compound 125 as defined in claim 1, a crystalline form or hydrate of the compound 125 maleate salt as defined in claim 3, or a crystal form of the compound 125 as free base as defined in claim 4.

6. A method for treating a disease selected from the group consisting of thymic carcinoma and melanoma in a mammal, comprising administering to said mammal a therapeutically effective amount of any salt of the compound 125 as defined in claim 1, a crystalline form or hydrate of the compound 125 maleate salt as defined in claim 3, or a crystal form of the compound 125 as free base as defined in claim 4.

* * * * *